United States Patent
Farritor et al.

(10) Patent No.: US 9,888,966 B2
(45) Date of Patent: Feb. 13, 2018

(54) METHODS, SYSTEMS, AND DEVICES RELATING TO FORCE CONTROL SURGICAL SYSTEMS

(71) Applicant: Board of Regents of the University of Nebraska, Lincoln, NE (US)

(72) Inventors: Shane Farritor, Lincoln, NE (US); Thomas Frederick, Omaha, NE (US); Kearney Lackas, Lincoln, NE (US); Joe Bartels, Lincoln, NE (US); Jacob Greenburg, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 14/210,934

(22) Filed: Mar. 14, 2014

(65) Prior Publication Data
US 2014/0371762 A1 Dec. 18, 2014

Related U.S. Application Data

(60) Provisional application No. 61/781,594, filed on Mar. 14, 2013.

(51) Int. Cl.
*A61B 34/30* (2016.01)
*A61B 19/00* (2006.01)
(Continued)

(52) U.S. Cl.
CPC .......... *A61B 19/2203* (2013.01); *A61B 34/30* (2016.02); *A61B 34/76* (2016.02);
(Continued)

(58) Field of Classification Search
CPC ........ A61B 19/2203; A61B 2019/2292; A61B 2019/464; A61B 2019/466; A61B 2019/2223; A61B 2019/223
(Continued)

(56) References Cited

U.S. PATENT DOCUMENTS 3,870,264 A 3/1975 Robinson
3,989,952 A 11/1976 Hohmann
(Continued)

FOREIGN PATENT DOCUMENTS

CN 1082821918 12/2012
DE 102010040405 3/2012
(Continued)

OTHER PUBLICATIONS

Patronik et al., "Development of a Tethered Epicardial Crawler for Minimally Invasive Cardiac Therapies," IEEE, pp. 239-240.
(Continued)

*Primary Examiner* — Katrina Stransky
(74) *Attorney, Agent, or Firm* — Davis, Brown, Koehn, Shors & Roberts, P.C.; Sean D. Solberg

(57) ABSTRACT

The various embodiments herein relate to robotic surgical systems and devices that use force and/or torque sensors to measure forces applied at various components of the system or device. Certain implementations include robotic surgical devices having one or more force/torque sensors that detect or measure one or more forces applied at or on one or more arms. Other embodiments relate to systems having a robotic surgical device that has one or more sensors and an external controller that has one or more motors such that the sensors transmit information that is used at the controller to actuate the motors to provide haptic feedback to a user.

20 Claims, 10 Drawing Sheets

(51) Int. Cl.
  *B25J 9/16*     (2006.01)
  *A61B 34/00*    (2016.01)
  *A61B 90/00*    (2016.01)

(52) U.S. Cl.
  CPC ....... *B25J 9/1602* (2013.01); *A61B 2090/064* (2016.02); *Y10S 901/27* (2013.01); *Y10S 901/46* (2013.01)

(58) Field of Classification Search
  USPC .......................................................... 606/130
  See application file for complete search history.

(56) References Cited

U.S. PATENT DOCUMENTS

| | | | |
|---|---|---|---|
| 4,246,661 A | 1/1981 | Pinson | |
| 4,258,716 A | 3/1981 | Sutherland | |
| 4,278,077 A | 7/1981 | Mizumoto | |
| 4,538,594 A | 9/1985 | Boebel et al. | |
| 4,568,311 A | 2/1986 | Miyaki | |
| 4,623,183 A | 11/1986 | Amori | |
| 4,736,645 A | 4/1988 | Zimmer | |
| 4,771,652 A | 9/1988 | Zimmer | |
| 4,852,391 A | 8/1989 | Ruch et al. | |
| 4,896,015 A | 1/1990 | Taboada et al. | |
| 4,897,014 A | 1/1990 | Tietze | |
| 4,922,755 A | 5/1990 | Oshiro et al. | |
| 4,922,782 A | 5/1990 | Kawai | |
| 4,990,050 A | 2/1991 | Tsuge et al. | |
| 5,019,968 A | 5/1991 | Wang et al. | |
| 5,108,140 A | 4/1992 | Bartholet | |
| 5,172,639 A | 12/1992 | Wiesman et al. | |
| 5,176,649 A | 1/1993 | Wakabayashi | |
| 5,178,032 A | 1/1993 | Zona et al. | |
| 5,187,032 A | 2/1993 | Sasaki et al. | |
| 5,187,796 A | 2/1993 | Wang et al. | |
| 5,195,388 A | 3/1993 | Zona et al. | |
| 5,201,325 A | 4/1993 | McEwen et al. | |
| 5,217,003 A | 6/1993 | Wilk | |
| 5,263,382 A | 11/1993 | Brooks et al. | |
| 5,271,384 A | 12/1993 | McEwen et al. | |
| 5,284,096 A | 2/1994 | Pelrine et al. | |
| 5,297,443 A | 3/1994 | Wentz | |
| 5,297,536 A | 3/1994 | Wilk | |
| 5,304,899 A | 4/1994 | Sasaki et al. | |
| 5,307,447 A | 4/1994 | Asano et al. | |
| 5,353,807 A | 10/1994 | DeMarco | |
| 5,363,935 A | 11/1994 | Schempf et al. | |
| 5,382,885 A | 1/1995 | Salcudean et al. | |
| 5,388,528 A | 2/1995 | Pelrine et al. | |
| 5,436,542 A | 7/1995 | Petelin et al. | |
| 5,441,494 A | 8/1995 | Ortiz | |
| 5,458,131 A | 10/1995 | Wilk | |
| 5,458,583 A | 10/1995 | McNeely et al. | |
| 5,458,598 A | 10/1995 | Feinberg et al. | |
| 5,471,515 A | 11/1995 | Fossum et al. | |
| 5,515,478 A | 5/1996 | Wang | |
| 5,524,180 A | 6/1996 | Wang et al. | |
| 5,553,198 A | 9/1996 | Wang et al. | |
| 5,562,448 A | 10/1996 | Mushabac | |
| 5,588,442 A | 12/1996 | Scovil et al. | |
| 5,620,417 A | 4/1997 | Jang et al. | |
| 5,623,582 A | 4/1997 | Rosenberg | |
| 5,624,380 A | 4/1997 | Takayama et al. | |
| 5,624,398 A | 4/1997 | Smith et al. | |
| 5,632,761 A | 5/1997 | Smith et al. | |
| 5,645,520 A | 7/1997 | Nakamura et al. | |
| 5,657,429 A | 8/1997 | Wang et al. | |
| 5,657,584 A | 8/1997 | Hamlin | |
| 5,672,168 A | 9/1997 | de la Torre et al. | |
| 5,674,030 A | 10/1997 | Sigel | |
| 5,728,599 A | 3/1998 | Rosteker et al. | |
| 5,736,821 A | 4/1998 | Suyama et al. | |
| 5,754,741 A | 5/1998 | Wang et al. | |
| 5,762,458 A | 6/1998 | Wang et al. | |
| 5,769,640 A | 6/1998 | Jacobus et al. | |
| 5,791,231 A | 8/1998 | Cohn et al. | |
| 5,792,135 A | 8/1998 | Madhani et al. | |
| 5,797,538 A | 8/1998 | Heaton et al. | |
| 5,797,900 A | 8/1998 | Madhani et al. | |
| 5,807,377 A | 9/1998 | Madhani et al. | |
| 5,808,665 A | 9/1998 | Green | |
| 5,815,640 A | 9/1998 | Wang et al. | |
| 5,825,982 A | 10/1998 | Wright et al. | |
| 5,841,950 A | 11/1998 | Wang et al. | |
| 5,845,646 A | 12/1998 | Lemelson | |
| 5,855,583 A | 1/1999 | Wang et al. | |
| 5,876,325 A | 3/1999 | Mizuno et al. | |
| 5,878,193 A | 3/1999 | Wang et al. | |
| 5,878,783 A | 3/1999 | Smart | |
| 5,895,417 A | 4/1999 | Pomeranz et al. | |
| 5,906,591 A | 5/1999 | Dario et al. | |
| 5,907,664 A | 5/1999 | Wang et al. | |
| 5,910,129 A | 6/1999 | Koblish et al. | |
| 5,911,036 A | 6/1999 | Wright et al. | |
| 5,971,976 A | 10/1999 | Wang et al. | |
| 5,993,467 A | 11/1999 | Yoon | |
| 6,001,108 A | 12/1999 | Wang et al. | |
| 6,007,550 A | 12/1999 | Wang et al. | |
| 6,030,365 A | 2/2000 | Laufer | |
| 6,031,371 A | 2/2000 | Smart | |
| 6,058,323 A | 5/2000 | Lemelson | |
| 6,063,095 A | 5/2000 | Wang et al. | |
| 6,066,090 A | 5/2000 | Yoon | |
| 6,102,850 A | 8/2000 | Wang et al. | |
| 6,107,795 A | 8/2000 | Smart | |
| 6,132,368 A | 10/2000 | Cooper | |
| 6,132,441 A | 10/2000 | Grace | |
| 6,139,563 A | 10/2000 | Cosgrove, III et al. | |
| 6,156,006 A | 12/2000 | Brosens et al. | |
| 6,159,146 A | 12/2000 | El Gazayerli | |
| 6,162,171 A | 12/2000 | Ng et al. | |
| D438,617 S | 3/2001 | Cooper et al. | |
| 6,206,903 B1 | 3/2001 | Ramans | |
| D441,076 S | 4/2001 | Cooper et al. | |
| 6,223,100 B1 | 4/2001 | Green | |
| D441,862 S | 5/2001 | Cooper et al. | |
| 6,238,415 B1 | 5/2001 | Sepetka et al. | |
| 6,240,312 B1 | 5/2001 | Alfano et al. | |
| 6,241,730 B1 | 6/2001 | Alby | |
| 6,244,809 B1 | 6/2001 | Wang et al. | |
| 6,246,200 B1 | 6/2001 | Blumenkranz et al. | |
| D444,555 S | 7/2001 | Cooper et al. | |
| 6,286,514 B1 | 9/2001 | Lemelson | |
| 6,292,678 B1 | 9/2001 | Hall et al. | |
| 6,293,282 B1 | 9/2001 | Lemelson | |
| 6,296,635 B1 | 10/2001 | Smith et al. | |
| 6,309,397 B1 | 10/2001 | Julian et al. | |
| 6,309,403 B1 | 10/2001 | Minor et al. | |
| 6,312,435 B1 | 11/2001 | Wallace et al. | |
| 6,321,106 B1 | 11/2001 | Lemelson | |
| 6,327,492 B1 | 12/2001 | Lemelson | |
| 6,331,181 B1 | 12/2001 | Tierney et al. | |
| 6,346,072 B1 | 2/2002 | Cooper | |
| 6,352,503 B1 | 3/2002 | Matsui et al. | |
| 6,364,888 B1 | 4/2002 | Niemeyer et al. | |
| 6,371,952 B1 | 4/2002 | Madhani et al. | |
| 6,394,998 B1 | 5/2002 | Wallace et al. | |
| 6,398,726 B1 | 6/2002 | Ramans et al. | |
| 6,400,980 B1 | 6/2002 | Lemelson | |
| 6,408,224 B1 | 6/2002 | Okamoto et al. | |
| 6,424,885 B1 | 7/2002 | Niemeyer et al. | |
| 6,432,112 B2 | 8/2002 | Brock et al. | |
| 6,436,107 B1 | 8/2002 | Wang et al. | |
| 6,441,577 B2 | 8/2002 | Blumenkranz et al. | |
| 6,450,104 B1 | 9/2002 | Grant et al. | |
| 6,451,027 B1 | 9/2002 | Cooper et al. | |
| 6,454,758 B1 | 9/2002 | Thompson et al. | |
| 6,459,926 B1 | 10/2002 | Nowlin et al. | |
| 6,463,361 B1 | 10/2002 | Wang et al. | |
| 6,468,203 B2 | 10/2002 | Belson | |
| 6,468,265 B1 | 10/2002 | Evans et al. | |
| 6,470,236 B2 | 10/2002 | Ohtsuki | |
| 6,491,691 B1 | 12/2002 | Morley et al. | |

(56) References Cited

U.S. PATENT DOCUMENTS

| | | |
|---|---|---|
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sproul |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |

(56) References Cited

U.S. PATENT DOCUMENTS

| | | |
|---|---|---|
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 8,604,742 B2 | 12/2013 | Farritor et al. |
| 9,089,353 B2 | 7/2015 | Farritor |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zadno-Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1* | 7/2003 | Wang ............... A61B 19/22 606/1 |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | Arnault De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Jacobsen et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena Alejandro |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |

(56) References Cited

U.S. PATENT DOCUMENTS

| | | | |
|---|---|---|---|
| 2009/0248038 A1* | 10/2009 | Blumenkranz | A61B 19/2203 606/130 |
| 2009/0281377 A1 | 11/2009 | Newell et al. | |
| 2009/0305210 A1 | 12/2009 | Guru et al. | |
| 2010/0010294 A1 | 1/2010 | Conlon et al. | |
| 2010/0016659 A1 | 1/2010 | Weitzner et al. | |
| 2010/0016853 A1 | 1/2010 | Burbank | |
| 2010/0042097 A1 | 2/2010 | Newton et al. | |
| 2010/0056863 A1 | 3/2010 | Dejima et al. | |
| 2010/0069710 A1 | 3/2010 | Yamatani et al. | |
| 2010/0069940 A1 | 3/2010 | Miller et al. | |
| 2010/0081875 A1 | 4/2010 | Fowler et al. | |
| 2010/0139436 A1 | 6/2010 | Kawashima et al. | |
| 2010/0198231 A1 | 8/2010 | Scott | |
| 2010/0204713 A1 | 8/2010 | Ruiz Morales | |
| 2010/0245549 A1 | 9/2010 | Allen et al. | |
| 2010/0262162 A1 | 10/2010 | Omori | |
| 2010/0292691 A1 | 11/2010 | Brogna | |
| 2010/0318059 A1 | 12/2010 | Farritor et al. | |
| 2011/0015569 A1 | 1/2011 | Kirschenman et al. | |
| 2011/0020779 A1 | 1/2011 | Hannaford et al. | |
| 2011/0071347 A1* | 3/2011 | Rogers | A61B 1/00149 600/104 |
| 2011/0071544 A1 | 3/2011 | Steger et al. | |
| 2011/0077478 A1 | 3/2011 | Freeman et al. | |
| 2011/0082365 A1 | 4/2011 | McGrogan et al. | |
| 2011/0098529 A1 | 4/2011 | Ostrovsky et al. | |
| 2011/0152615 A1* | 6/2011 | Schostek | A61B 19/2203 600/111 |
| 2011/0224605 A1 | 9/2011 | Farritor et al. | |
| 2011/0230894 A1 | 9/2011 | Simaan et al. | |
| 2011/0237890 A1 | 9/2011 | Farritor et al. | |
| 2011/0238080 A1 | 9/2011 | Ranjit et al. | |
| 2011/0264078 A1 | 10/2011 | Lipow | |
| 2011/0270443 A1 | 11/2011 | Kamiya et al. | |
| 2012/0035582 A1 | 2/2012 | Nelson et al. | |
| 2012/0109150 A1 | 5/2012 | Quaid et al. | |
| 2012/0116362 A1 | 5/2012 | Kieturakis | |
| 2012/0179168 A1 | 7/2012 | Farritor | |
| 2012/0253515 A1 | 10/2012 | Coste-Maniere et al. | |
| 2013/0041360 A1 | 2/2013 | Farritor | |
| 2013/0131695 A1 | 5/2013 | Scarfogliero et al. | |
| 2013/0345717 A1 | 12/2013 | Markvicka et al. | |
| 2014/0046340 A1 | 2/2014 | Wilson et al. | |
| 2014/0058205 A1 | 2/2014 | Frederick et al. | |
| 2014/0039515 A1 | 6/2014 | Mondry et al. | |
| 2014/0303434 A1 | 10/2014 | Farritor et al. | |
| 2015/0051446 A1 | 2/2015 | Farritor et al. | |

FOREIGN PATENT DOCUMENTS

| | | | |
|---|---|---|---|
| EP | 1354670 | 10/2003 | |
| EP | 2286756 | 2/2011 | |
| EP | 2286756 A1 | 2/2011 | |
| EP | 2329787 | 8/2011 | |
| EP | 2563261 | 3/2013 | |
| JP | 2004144533 | 5/1990 | |
| JP | 5115425 | 5/1993 | |
| JP | 200716235 | 6/1993 | |
| JP | 6-508049 | 9/1994 | |
| JP | 2006507809 | 9/1994 | |
| JP | 2006508049 | 9/1994 | |
| JP | 07 136173 | 5/1995 | |
| JP | 7306155 | 11/1995 | |
| JP | 08-224248 | 9/1996 | |
| JP | 2001505810 | 5/2001 | |
| JP | 2003220065 | 8/2003 | |
| JP | 2004144533 | 5/2004 | |
| JP | 2004322310 | 6/2004 | |
| JP | 2004180781 | 7/2004 | |
| JP | 2004322310 | 11/2004 | |
| JP | 2004329292 | 11/2004 | |
| JP | 2009-106606 | 5/2009 | |
| JP | 2010-533045 | 10/2010 | |
| JP | 2010-536436 | 12/2010 | |
| JP | 2010536436 | 12/2010 | |
| JP | 2011-504794 | 2/2011 | |
| JP | 2011-045500 | 3/2011 | |
| JP | 2011-115591 | 6/2011 | |
| WO | WO 92/21291 | 5/1991 | |
| WO | WO 0189405 | 11/2001 | |
| WO | WO 02/082979 | 10/2002 | |
| WO | WO 02/100256 | 12/2002 | |
| WO | WO 2005/009211 | 7/2004 | |
| WO | WO 2005009211 | 2/2005 | |
| WO | WO 2005044095 | 5/2005 | |
| WO | WO 2006/052927 | 8/2005 | |
| WO | WO 2006 005075 | 1/2006 | |
| WO | WO 2006/079108 | 1/2006 | |
| WO | WO2006079108 | 7/2006 | |
| WO | WO 2007011654 | 1/2007 | |
| WO | WO 2007/111571 | 10/2007 | |
| WO | WO 2007/149559 | 12/2007 | |
| WO | WO 2009023851 A1 | 2/2009 | |
| WO | WO 2009/144729 | 12/2009 | |
| WO | WO2010/042611 | 4/2010 | |
| WO | WO2010/046823 | 4/2010 | |
| WO | 2010050771 | 5/2010 | |
| WO | WO2010050771 A2 | 5/2010 | |
| WO | WO 2011075693 | 6/2011 | |
| WO | 2011118646 | 9/2011 | |
| WO | WO 2011/118646 A1 | 9/2011 | |
| WO | WO 2011/135503 A1 | 11/2011 | |
| WO | WO 2011135503 | 11/2011 | |
| WO | WO 2011135503 A1 * | 11/2011 | A61B 19/2203 |
| WO | WO 2013009887 | 1/2013 | |
| WO | WO 2014011238 | 1/2014 | |

OTHER PUBLICATIONS

Patronik et al., "Crawling on the Heart: A Mobile Robotic Device for Minimally Invasive Cardiac Interventions," MICCAI, 2004, pp. 9-16.

Patronik et al., "Preliminary evaluation of a mobile robotic device for navigation and intervention on the beating heart," Computer Aided Surgery, 10(4): 225-232, Jul. 2005.

Peirs et al., "A miniature manipulator for integration in a self-propelling endoscope," Sensors and Actuators A, 2001, 92: 343-349.

Peters, "Minimally Invasive Colectomy: Are the Potential Benefits Realized?" Dis Colon Rectum 1993; 36: 751-756.

Phee et al., "Analysis and Development of Locomotion Devices for the Gastrointestinal Tract," IEEE Transaction on Biomedical Engineering, vol. 49, No. 6, Jun. 2002, pp. 613-616.

Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.

Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.

Preliminary Amendment filed Apr. 11, 2007, in related case U.S. Appl. No. 11/403,756, 7 pp.

Preliminary Amendment filed Jul. 30, 2008, in related case U.S. Appl. No. 12/171,413, 4 pp.

RCE and Amendment filed Jun. 13, 2007, in related case U.S. Appl. No. 11/403,756, 8 pp.

Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.

Rentschler et al., Mobile In Vivo Biopsy Robot, IEEE International Conference on Robotics and Automation, Orlando, Florida, May 2006, pp. 4155-4160.

Rentschler et al., "Miniature in vivo Robots for Remote and Harsh Environments," IEEE Transactions on Information Technology in Biomedicine, Jan. 2006; 12(1): 66-75.

(56) References Cited

OTHER PUBLICATIONS

Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al.., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mechanical Design of Robotic In Vivo Wheeled Mobility," ASME Journal of Mechanical Design, 2006a, pp, I-II.
Rentschler et al., "Mobile In Vivo Camera Robots Provide Sole Visual Feedback for Abdominal Exploration and Cholecystectomy," Journal of Surgical Endoscopy, 20-I: 135-138, 2006b.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Infornnatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Informatics—Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Informatics—Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue Dragon—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
International Preliminary Report on Patentability from related case PCT/US2007/014567, dated Jan. 8, 2009, 11 pp.
International Search report and Written Opinion from international application No. PCT/US2012/41911, dated Mar. 13, 2013.
International Search Report and Written Opinion from international application No. PCT/US12/46274, dated Sep. 25, 2012.
International Search Report and Written Opinion from international application No. PCT/US2007/089191, dated Nov. 10, 2008, 20 pp.
"International Search Report and Written Opinion from international application No. PCT/US07/14567, dated Apr. 28, 2008, 19 pp."
International Search Report and Written Opinion of international application No. PCT/US2008/069822, dated Aug. 5, 2009, 12 pp.
International Search Report and Written Opinion of international application No. PCT/US2008/073334, dated Jan. 12, 2009, 11 pp.
International Search Report and Written Opinion of international application No. PCT/US2008/073369, dated Nov. 12, 2008, 12 pp.
International Search Report and Written Opinion issued in PCT/US11/46809, dated Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.

(56) References Cited

OTHER PUBLICATIONS

Kazemier et al. (1998), "Vascular Injuries During Laparoscopy," J. Am. Coli. Surg. 186(5): 604-5.

Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.

Ko et al., "Per-Oral transgastric abdominal surgery," Chinese Journal of Digestive Diseases, 2006; 7: 67-70.

Lafullarde et al., "Laparoscopic Nissen Fundoplication: Five-year Results and Beyond," Arch/Surg, Feb. 2001; 136:180-184.

Leggett et al. (2002), "Aortic injury during laparoscopic fundoplication," Surg. Endoscopy 16(2): 362.

Li et al. (2000), "Microvascular Anastomoses Performed in Rats Using a Microsurgical Telemanipulator," Comp. Aid. Surg. 5: 326-332.

Liem et al., "Comparison of Conventional Anterior Surgery and Laparoscopic Surgery for Inguinal-hernia Repair," New England Journal of Medicine, 1997; 336 (22): 1541-1547.

MacFarlane et al., "Force-Feedback Grasper Helps Restore the Sense of Touch in Minimally Invasive Surgery," Journal of Gastrointestinal Surgery, 1999; 3: 278-285.

Mack et al., "Present Role of Thoracoscopy in the Diagnosis and Treatment of Diseases of the Chest," Ann Thorac Surgery, 1992; 54: 403-409.

Mack, "Minimally Invasive and Robotic Surgery," JAMA, Feb. 2001; 285(5): 568-572.

Mei et al., "Wireless Drive and Control of a Swimming Microrobot," Proceedings of the 2002 IEEE International Conference on Robotics & Automation, May 2002: 1131-1136.

Melvin et al., "Computer-Enhanced vs. Standard Laparoscopic Antireflux Surgery," J Gastrointest Surg 2002; 6: 11-16.

Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.

Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.

Menciassi et al., "Shape memory alloy clamping devices of a capsule for monitoring tasks in the gastrointestinal tract," J. Micromech. Microeng, 2005, 15: 2045-2055.

Meron, "The development of the swallowable video capsule (M2A)," Gastrointestinal Endoscopy 2000; 52 6: 817-819.

Micron, http://www.micron.com, 2006, I/4-inch VGA NTSC/PAL CMOS Digital Image Sensor, 98 pp.

Midday Jeff et al., "Material Handling System for Robotic natural Orifice Surgery", Proceedings of the 2011 Design of medical Devices Conference, Apr. 12-14, 2011, Minneapolis, MN, 4 pages.

Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.

Munro (2002), "Laparoscopic access: complications, technologies, and techniques," Curro Opin. Obstet. Gynecol., 14(4): 365-74.

Nio et al., "Efficiency of manual vs robotical (Zeus) assisted laparoscopic surgery in the performance of standardized tasks," Surg Endosc, 2002; 16: 412-415.

Office Action dated Apr. 17, 2007, received in related case U.S. Appl. No. 11/552,379, 5 pp.

Office Action dated Apr. 3, 2009, received in related case U.S. Appl. No. 11/932,516, 43 pp.

Office Action dated Aug. 18, 2006, received in related case U.S. Appl. No. 11/398,174, 6 pp.

Office Action dated Aug. 21, 2006, received in related case U.S. Appl. No. 11/403,756, 6 pp.

Office Action dated Oct. 29, 2007, received in related case U.S. Appl. No. 11/695,944, 6 pp.

Office Action dated Oct. 9, 2008, received in related case U.S. Appl. No. 11/932,441, 4 pp.

Oleynikov et al., "In Vivo Camera Robots Provide Improved Vision for Laparoscopic Surgery," Computer Assisted Radiology and Surgery (CARS), Chicago, IL, Jun. 23-26, 2004b.

Oleynikov et al., "In Vivo Robotic Laparoscopy," Surgical Innovation, Jun. 2005, 12(2): 177-181.

Oleynikov et al., "Miniature Robots Can Assist in Laparoscopic Cholecystectomy," Journal of Surgical Endoscopy, 19-4: 473-476, 2005.

O'Neill, "Surgeon takes new route to gallbladder," The Oregonian, Jun. 2007, 2 pp.

Orlando et al., (2003), "Needle and Trocar Injuries in Diagnostic Laparoscopy under Local Anesthesia: What is the True Incidence of These Complications?" Journal of Laparoendoscopic & Advanced Surgical Techniques 13(3): 181-184.

Park et al., "Trocar-less Instrumentation for Laparoscopy: Magnetic Positioning of Intra-abdominal Camera and Retractor," Ann Surg, Mar. 2007; 245(3): 379-384.

Park et al., "Experimental studies of transgastric gallbladder surgery: cholecystectomy and cholecystogastric anastomosis (videos)," Gastrointestinal Endoscopy, 2005; 61(4): 601-606.

Palm, William, "Rapid Prototyping Primer" May 1998 (revised Jul. 30, 2002) (http://www.me.psu.edu/lamancusa/rapidpro/primer/chapter2.htm).

Guo et al., "Micro Active Guide Wire Catheter System—Characteristic Evaluation, Electrical Model and Operability Evaluation of Micro Active Catheter," Proceedings of the 1996 IEEE International Conference on Robotics and Automation, Apr. 1996: 2226-2231.

Guo et al., "Fish-like Underwater Microrobot with 3 DOF," Proceedings of the 2002 IEEE International Conference on Robotics & Automation, May 2002: 738-743.

Tendick et al., "Applications of Micromechatronics in Minimally Invasive Surgery," IEEE/ASME Transactions on Mechatronics, 1998; 3(1): 34-42.

Thomann et al., "The Design of a new type of Micro Robot for the Intestinal Inspection," Proceedings of the 2002 IEEE Intl. Conference on Intelligent Robots and Systems, Oct. 2002: 1385-1390.

U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.

Way et al., (editors), "Fundamentals of Laparoscopic Surgery," Churchill Livingstone Inc., 1995, 14 pp.

Wolfe et al., "Endoscopic Cholecystectomy: An analysis of Complications," Arch. Surg. Oct. 1991; 126: 1192-1196.

Worn et al., "Espirit Project No. 33915: Miniaturised Robot for Micro Manipulation (MINIMAN)", Nov. 1998; http://www.ipr.ira.ujka.de/-microbot/miniman.

Yu et al., "Microrobotic Cell Injection," Proceedings of the 2001 IEEE International Conference on Robotics and Automation, May 2001; 620-625.

Yu, BSN, RN, "M2ATM Capsule Endoscopy a Breakthrough Diagnostic Tool for Small Intestine Imagining," vol. 25, No. 1, Gastroenterology Nursing, pp. 24-27.

International Search Report and Written Opinion of international application No. PCT/US2010/061137, dated Feb. 11, 2011, 10 pp.

Abbou et al., "Laparoscopic Radical Prostatectomy with a Remote Controlled Robot," The Journal of Urology, Jun. 2001, 165: 1964-1966.

Glukhovsky et al.., "The development and application of wireless capsule endoscopy," Int. J. Med. Robot. Comput. Assist. Surgery, 2004; I (1): 114-123.

Gong et al., Wireless endoscopy, Gastrointestinal Endoscopy 2000; 51(6): 725-729.

Hanly et al., "Value of the SAGES Learning Center in introducing new technology," Surgical Endoscopy, 2004; 19 (4): 477-483.

(56) References Cited

OTHER PUBLICATIONS

Hanly et al., "Robotic Abdominal Surgery," The American Journal of Surgery 188 (Suppl.to Oct. 1994): 19S-26S, 2004.
Heikkinen et al., "Comparison of laparoscopic and open Nissen fundoplication two years after operation: A prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.
Horgan et al., "Technical Report: Robots in Laparoscopic Surgery," Journal of Laparoendoscopic & Advanced Surgical Techniques, 2001; 11(6): 415-419.
Stoianovici et al., "Robotic Tools for Minimally Invasive Urologic Surgery", Jan. 1, 2002, pp. 1-17.
Cleary et al., "State of the Art in Surgical Rootics: Clinical Applications and Technology Challenges", "Computer Aided Surgery", Jan. 1, 2002, pp. 312-328, vol. 6.
Green, "Telepresence Surgery", Jan. 1, 1995, Publisher: IEEE Engineering in Medicine and Biology.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving In Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6).
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
Guber et al., "Miniaturized Instrumetn Systems for Minimally Invasive Diagnosis and Therapy," Biomedizinishe Technic. 2002, Band 47, Erganmngsband 1: 2, p. 198, 4 p. Jan. 2002, vol. 47 Issue 1-2, p. 198, 4 p.

\* cited by examiner

METHODS, SYSTEMS, AND DEVICES RELATING TO FORCE CONTROL SURGICAL SYSTEMS

CROSS-REFERENCE TO RELATED APPLICATION(S)

This application claims priority to U.S. Provisional Application 61/781,594, filed on Mar. 14, 2013 and entitled "Methods, Systems, and Devices Relating to Force Control Surgical Systems," which is hereby incorporated herein by reference in its entirety.

GOVERNMENT SUPPORT

This invention was made with government support under Grant No. DGE-10410000 awarded by the National Science Foundation; Grant Nos. NNX09AO71A and NNX10AJ26G awarded by the National Aeronautics and Space Administration; and Grant No. W81XWF-09-2-0185 awarded by U.S. Army Medical Research and Materiel Command within the Department of Defense. Accordingly, the government has certain rights in this invention.

FIELD OF THE INVENTION

The various embodiments disclosed herein relate to robotic surgical systems and devices that use force and/or torque sensors to measure forces applied at various components of the system or device. Some exemplary implementations relate to various robotic surgical devices having one or more force/torque sensors that detect or measure one or more forces applied at or on one or more arms. Other embodiments relate to various systems that have a robotic surgical device and a controller, wherein the device has one or more sensors and the controller has one or more motors such that the sensors transmit information that is used at the controller to actuate the motors to provide haptic feedback to a user.

BACKGROUND OF THE INVENTION

Robotic surgical systems have surgical robotic devices or components positioned within a target cavity of a patient such that one or more arms or other components of such a device are configured to perform a procedure within the cavity. In these systems, an external controller is operably coupled to the surgical device such that a user can control or manipulate the device within the patient's cavity via the external controller. One disadvantage of such systems is the lack of tactile feedback for the user during the procedure. That is, the surgeon cannot "feel" the amount of force being applied by or on the arms or components of the surgical device within the patient's cavity in the same way that a surgeon would get some tactile feedback using standard laparoscopic tools (involving long tools inserted through trocars that are positioned into the cavity through incisions).

There is a need in the art for improved robotic surgical systems that can detect and/or measure forces applied at or on robotic surgical devices positioned within a patient and/or provide haptic feedback to the user at the external controller.

BRIEF SUMMARY OF THE INVENTION

Discussed herein are various robotic surgical devices, each having one or more force or torque sensors to measure force or torque applied to certain portions of the device. Additionally, surgical systems are also disclosed, each having an external controller that works in conjunction with sensors on a robotic surgical device to provide haptic feedback to a user.

In Example 1, a robotic surgical device comprises a device body configured to be positioned through an incision into a cavity of a patient, a first shoulder component operably coupled to the device body, a first arm operably coupled to the first shoulder component, and a force sensor operably coupled with the first arm. The first arm is configured to be positioned entirely within the cavity of the patient. The force sensor is positioned to measure an amount of force applied by the first arm.

Example 2 relates to the robotic surgical device according to Example 1, wherein the force sensor is disposed between the device body and the first shoulder component.

Example 3 relates to the robotic surgical device according to Example 1, wherein the force sensor is disposed on the first arm.

Example 4 relates to the robotic surgical device according to Example 3, wherein the first arm comprises an upper arm component and a forearm component, wherein the force sensor is disposed on the forearm component.

Example 5 relates to the robotic surgical device according to Example 1, wherein the first arm comprises an upper arm component and a forearm component, wherein the forearm component is operably coupled to the upper arm component at an elbow joint, wherein the forearm component comprises a link operably coupled at a distal end to the force sensor and operably coupled at a proximal end to an elbow joint.

Example 6 relates to the robotic surgical device according to Example 5, further comprising an interface plate disposed between the force sensor and the link.

Example 7 relates to the robotic surgical device according to Example 1, wherein the force sensor is positioned to measure the amount of force applied at a distal-most point on the first arm.

In Example 8, a robotic surgical system comprises a robotic surgical device configured to be positioned into a cavity of a patient through an incision, a processor, and a user controller operably coupled to the processor. The robotic surgical device comprises a device body, at least one arm operably coupled to the body, and at least one sensor operably coupled to the device. The processor is operably coupled to the at least one sensor. The user controller comprises a base, an upper arm component operably coupled to the base at a shoulder joint, a forearm component operably coupled to the upper arm component at an elbow joint, and a grasper operably coupled to the forearm component at a wrist joint. The shoulder joint comprises a first actuator operably coupled to the processor. The elbow joint comprises a second actuator operably coupled to the processor. The wrist joint comprises a third actuator operably coupled to the processor. The at least one sensor is configured to sense force or torque at the robotic surgical device and transmit force or torque information to the processor. The processor is configured to calculate the force or torque being applied at the robotic surgical device and transmit instructions to actuate at least one of the first, second, or third actuator based on the force or torque, thereby providing haptic feedback at the controller.

Example 9 relates to the robotic surgical system according to Example 8, wherein the at least one sensor is a force sensor operably coupled to the at least one arm.

Example 10 relates to the robotic surgical system according to Example 8, wherein the at least one sensor is a torque sensor operably coupled to a joint of the at least one arm.

Example 11 relates to the robotic surgical system according to Example 8, wherein the at least one sensor is a force sensor positioned between the device body and the at least one arm.

Example 12 relates to the robotic surgical system according to Example 8, wherein the at least one sensor is a force sensor disposed within the device body.

In Example 8, a robotic surgical device comprises a device body configured to be positioned through an incision into a cavity of a patient, a first arm operably coupled to the device body, a force sensor, and an end effector operably coupled to the actuator. The first arm comprises an actuator disposed within the first arm. Further, the first arm is configured to be positioned entirely within the cavity of the patient. The force sensor is operably coupled to the actuator. The end effector is positioned at a distal end of the first arm.

Example 14 relates to the robotic surgical device according to Example 13, further comprising a push/pull rod comprising a distal portion and a proximal portion, wherein the push/pull rod is operably coupled to the actuator at the proximal portion and further wherein the push/pull rod is operably coupled to the end effector at the distal portion.

Example 15 relates to the robotic surgical device according to Example 14, wherein the force sensor is disposed proximal to the actuator and is operably coupled to the proximal portion of the push/pull rod.

Example 16 relates to the robotic surgical device according to Example 14, wherein the end effector is a grasper, wherein the grasper comprises an open configuration when the push/pull rod is urged to a distal position, and further wherein the grasper comprises a closed configuration when the push/pull rod is urged to a proximal position.

Example 17 relates to the robotic surgical device according to Example 14, wherein the force sensor is operably coupled to the push/pull rod such that the force sensor is positioned along the length of the push/pull rod.

Example 18 relates to the robotic surgical device according to Example 13, wherein the end effector is a grasper.

Example 19 relates to the robotic surgical device according to Example 13, further comprising a shaft operably coupled to the end effector and a first gear operably coupled to the shaft, wherein the actuator comprises a second gear operably coupled to the first gear.

Example 20 relates to the robotic surgical device according to Example 19, wherein actuation of the actuator causes the shaft to rotate, thereby causing the end effector to rotate.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments herein relate to a surgical device configured to detect and measure the amount of force applied by the arm of the device. In certain embodiments, the surgical device is a robotic device with a robotic arm and at least one force sensor configured to detect the amount of force. In one embodiment, the force that is measured is the amount of force applied to the distal end of the robotic arm (also referred to herein as the "endpoint"). The information relating to the amount of force is then transmitted from the sensor to an external controller.

Figure 1A:
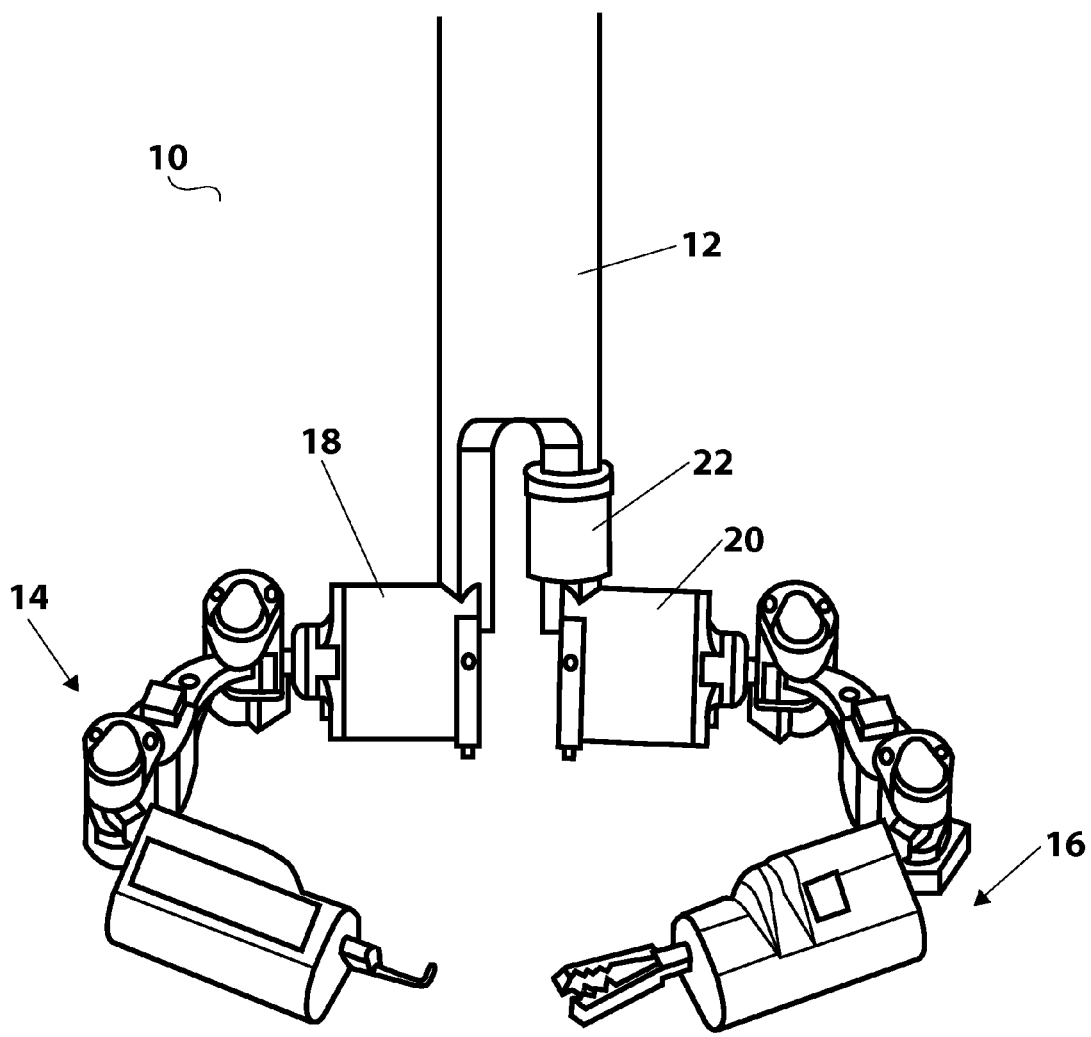
FIG. 1A is a perspective view of a robotic surgical device with a force sensor, according to one embodiment.
Figure 1B:
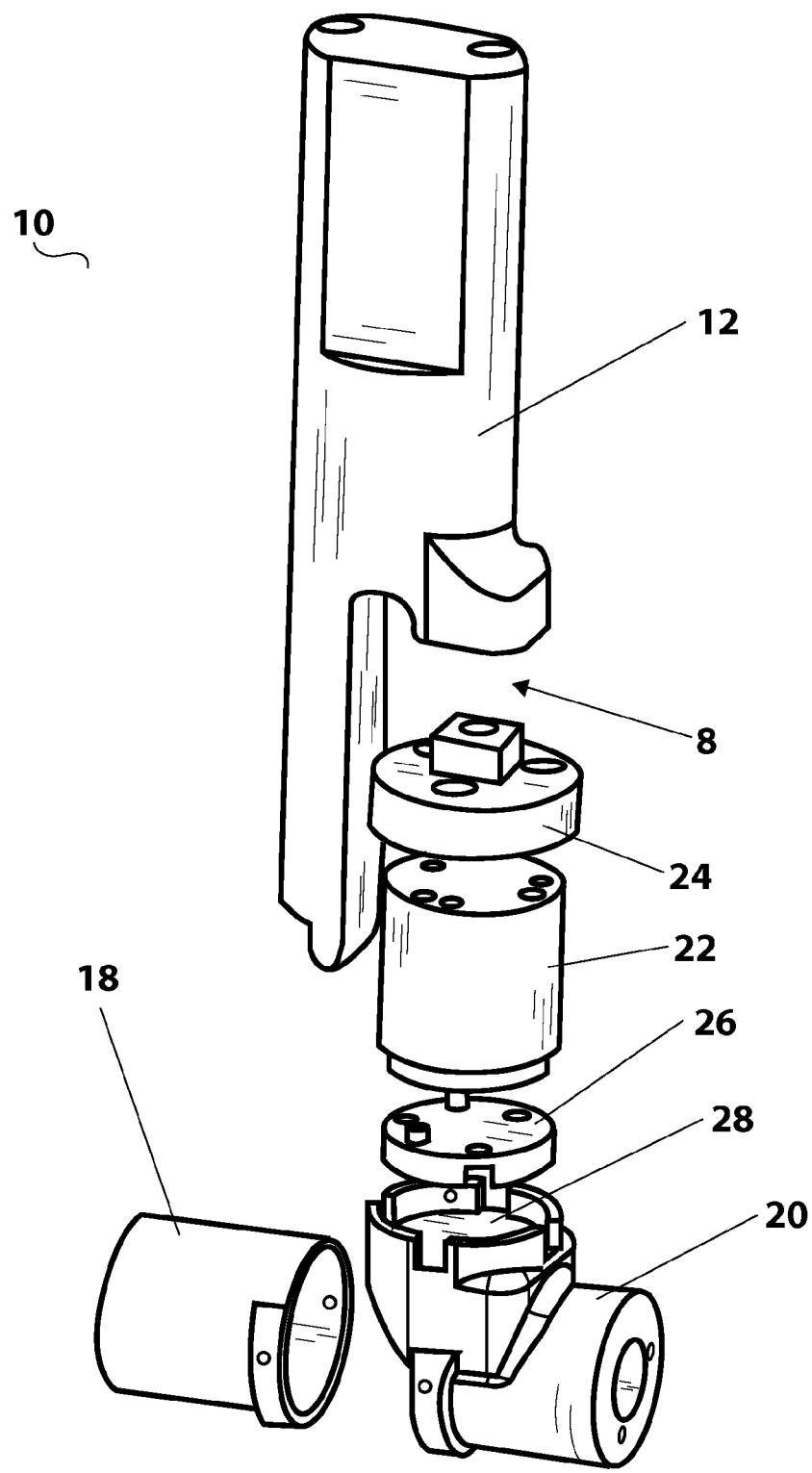
FIG. 1B is an exploded perspective view of a portion of the robotic surgical device of FIG. 1A.

FIGS. 1A and 1B depict one embodiment of a robotic surgical device 10 having a body 12 and two robotic arms 14, 16. The body 12 has two shoulders: a right shoulder 18 and a left shoulder 20. The right arm 14 is coupled to the right shoulder, and the left arm 16 is coupled to the left shoulder 20. In this implementation, the force sensor 22 is operably coupled to the body 12 between the body 12 and the left shoulder 20. As best shown in FIG. 1B, the distal portion of the body 12 in one embodiment has a recessed portion 8 defined therein as shown, and sensor 22 is positioned in the recessed portion 8 and coupled to the body 12 in that recessed portion 8.

Further, in certain implementations, the sensor 22 is coupled at its proximal end to a proximal connection component 24 and at its distal end to a distal connection component 26. In the embodiment depicted in FIG. 1B, the proximal connection component 24 is a proximal recessed component or proximal female connection component (also referred to herein as a "cup") 24 that is configured to receive and couple to the proximal end of the sensor. Further, the distal connection component 26 is a distal plate 26 have at least one projection (or "pin") 26A disposed on the proximal face of the plate 26 that is configured to mate with an appropriate opening (not shown) in the distal end of the sensor 22. In addition, the proximal connection component 24 has a projection 24A on its proximal face that is configured to mate with an appropriate opening (not shown) in the body 12. Plus, the distal plate 26 is configured to be received in a recessed portion or female connection 28 in the shoulder 20. In this embodiment, the proximal connection component 24 and distal connection component 26 can provide a substantially rigid coupling of the sensor 22 to the body 12 and shoulder 20. In alternative embodiments, the device 10 can have no shoulder components and the force sensor 22 can be positioned instead between the body 12 and the left arm 16 (rather than between the body 12 and the shoulder 20).

According to one implementation, this configuration results in the sensor 22 being positioned close to the incision in the patient when the device 10 is positioned correctly for purposes of a procedure. Given the position of the force sensor 22 proximal to the shoulder 20, it is understood that the sensor 22 will be subject to greater forces (due to the weight and length of the left arm 16) in comparison to a sensor positioned somewhere along or in a portion of the arm 16 itself. It is further understood that the position of the sensor 22 will also result in the sensor's 22 force detection being influenced by any forces applied anywhere along the length of the arm 16. The force sensor 22 is configured to detect and collect data relating to the amount of force being applied by the arm 16 during a procedure. In certain embodiments, the data is used to calculate the amount of force being applied at the most distal point on the arm 36 (the endpoint).

In one specific implementation, the force sensor 22 is a force torque sensor 22. Alternatively, the sensor 22 can be any known force or torque sensor as described in further detail elsewhere herein.

Figure 2:
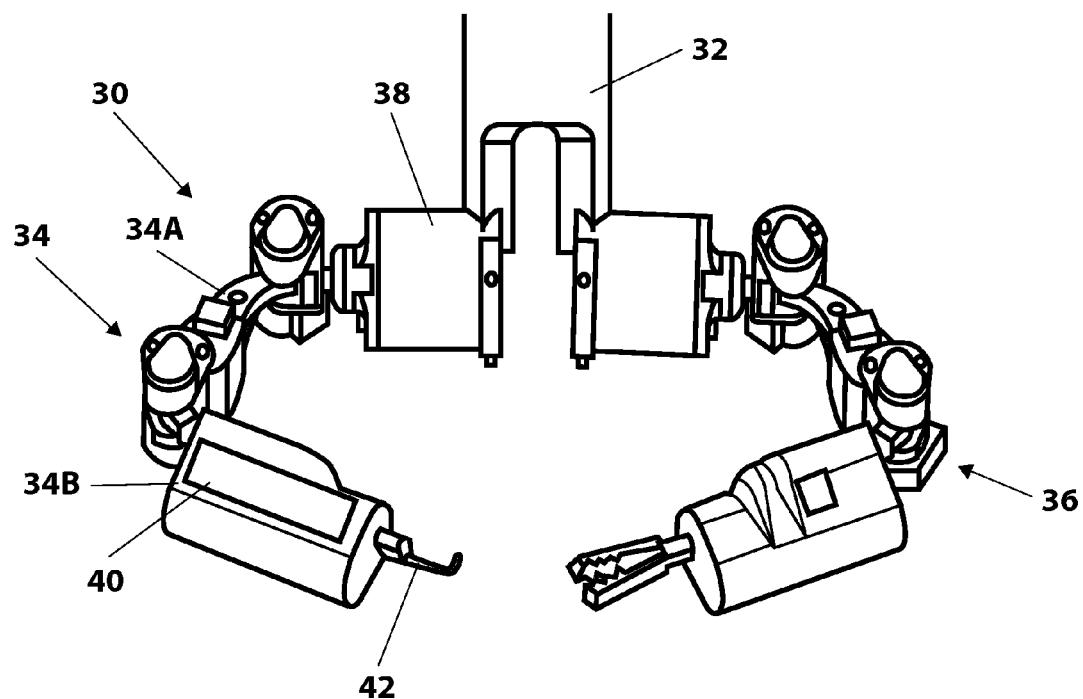
FIG. 2 is a perspective view of a robotic surgical device with a force sensor, according to another embodiment.

An alternative embodiment of a robotic device 30 with a force sensor 40 is depicted in FIG. 2. This device 30 also has a body 32 and right 34 and left 36 arms. This specific example is focused on the right arm 34, but it is understood that the description applies equally to the left arm 36 as well. In this particular implementation as shown, the sensor 40 is positioned near the distal end of the forearm 34B of the right arm 34. The proximity of the sensor 40 to the endpoint 42 (where the force is being measured) allows for the use of a smaller sensor 40 (due to the lesser forces being applied to the sensor 40 due to its position), thereby requiring less space in the forearm 34B and allowing for the possibility of a smaller forearm 34B. Further, according to one embodiment, the positioning of the force sensor 40 so close to the endpoint 42 eliminates the influence of any forces applied to the arm proximal to the sensor 40, thereby eliminating any irrelevant data created by such forces.

Alternatively, it is understood that the sensor 40 could be positioned anywhere on or within any of the components of either arm 34, 36 of this device 30 or any other device described or contemplated herein. For example, with respect to the right arm 34, a force sensor could be positioned within or on the right shoulder 38, the right upper arm 34A, or the right forearm 34B. Alternatively, the sensor could be positioned on or within any part of the left arm 36. Alternatively, the device 30 can have at least one sensor in each arm 34, 36. That is, in addition to the sensor 40 in the forearm 34B of the right arm 34, the device 30 can also have at least one sensor (not shown) on or in any component of the left arm 36. In a further alternative, each arm 34, 36 can have two or more sensors. In yet another implementation, the arms 34, 36 can each have multiple sensors such that the sensors detect and collect redundant data. The redundant data can then be filtered using known methods such as, but not limited to, Kalman filtering, to provide a more robust calculation of the forces being applied by the surgical device 30 to the tissue of the patient.

In one embodiment, the force sensor (such as force sensors 22 or 40) are force/torque sensors. According to another implementation, the force sensor is any sensor that can directly or indirectly measure the force at any point on the surgical device. Alternatively, any force sensor disclosed or contemplated herein can be any known sensor that can provide six degrees of force measurement. In another embodiment, the force sensor can be any known sensor that provides at least one dimension of force sensing. In a further alternative, the force sensor (including either of force sensors 22 or 40) can be a collection, group, arrangement, or set of two or more sensors that can provide six degrees of force measurement. In yet another alternative, the force information can be gathered by measuring the amount of torque at one or more of the joints of the arm of the device. For example, in one embodiment, the amount of torque can be measured at both the shoulder joint (between the shoulder 38 and the upper arm 34A) and the elbow joint (between the upper arm 34A and the forearm 34B) and that information can be used to calculate the amount of force being applied by the arm 34. In one implementation, the amount of torque is measured using any known torque sensor. Alternatively, the torque can be measured by measuring the motor current or be measuring the windup in the joint (or joints) by comparing absolute position sensor data to incremental position data. In a further alternative, the amount of joint torque can be measured using any other known method for measuring torque.

It is understood that any of the sensors disclosed or contemplated herein can be commercially available sensors or custom sensors. In accordance with one implementation, the force sensor is a known force/torque sensor called Nano17™, which is commercially available from ATI Industrial Automation, located in Apex, N.C. Alternatively, the sensor is a known reaction torque sensor called TFF400™, which is commercially available from Futek Advanced Sensor Technology, Inc., located in Irvine, Calif.

The force data collected by the force sensor(s) (or torque data collected by the torque sensor(s)) can be transmitted to a processor present in the robotic device (such as device 10 or 30) or in the external controller (not shown) and used to calculate the force being applied at the endpoint of the arm (or torque at the joint(s)). This will be described in further detail below. Known information relating to the dimensions of the robotic components and the kinematic arrangement of those components (such as the arm components) is incorporated into the calculation to determine the force at the endpoint (or torque at the joint(s)). Given that the calculation utilizes the dimensions of the components, the sensor(s) can be positioned anywhere along the robotic arm or even in the device body (as in FIG. 1) so long as the position is taken into account in the calculation.

Figure 3A:
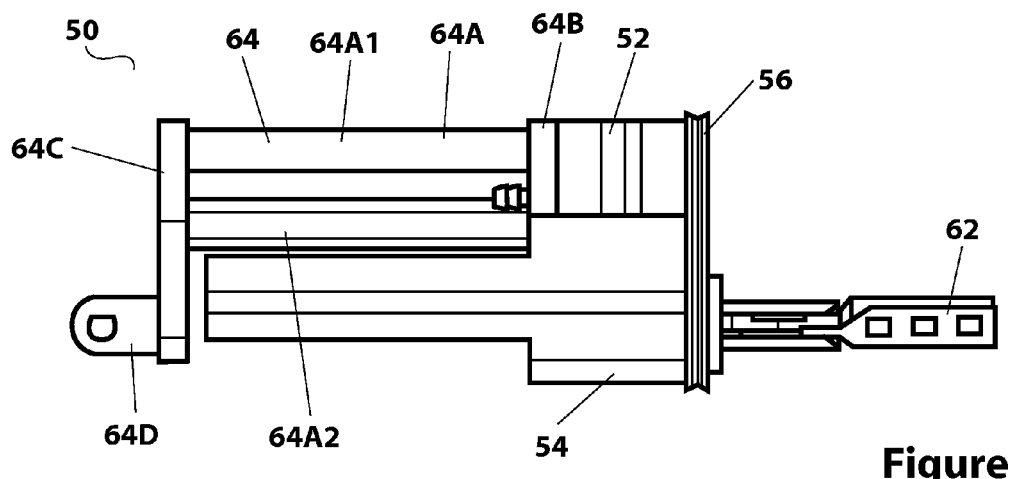
FIG. 3A is a side view of certain components of an arm of a robotic surgical device with a force sensor, according to one embodiment.
Figure 3B:
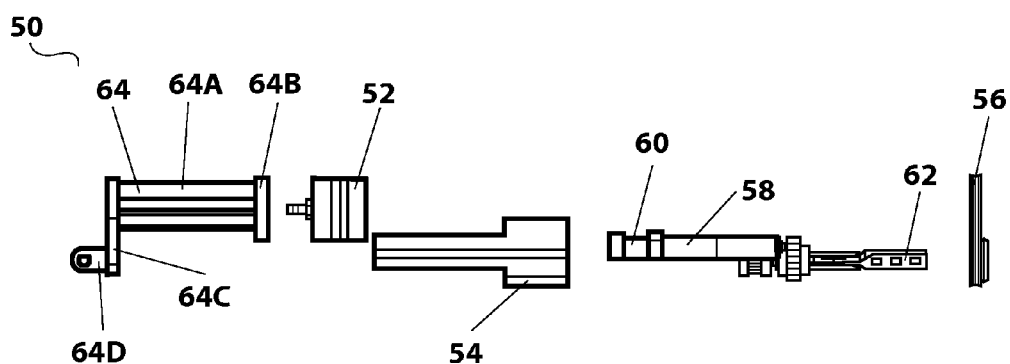
FIG. 3B is an exploded side view of certain components of the arm of FIG. 3A.
Figure 3C:
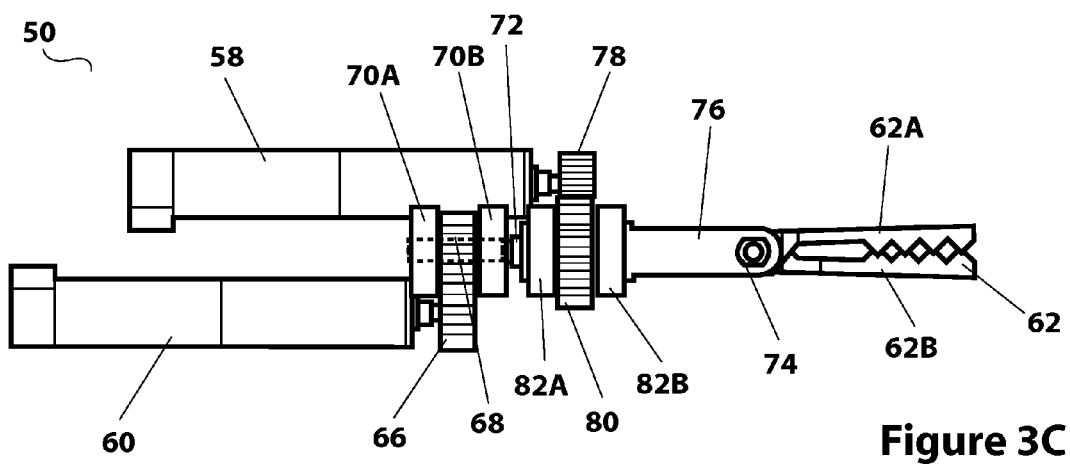
FIG. 3C is a side view of certain components of the arm of FIG. 3A.

FIGS. 3A, 3B, and 3C depict various aspects of a forearm 50 having a force sensor 52, according to another implementation. The forearm 50 has a motor housing 54, a front plate (also referred to herein as a "faceplate") 56, two motors 58, 60, and an end effector 62 which is a grasper tool 62. The motor housing 54 has the two motors 58, 60 at least partially disposed therein and is coupled at its distal end to the front plate 56. The forearm 50 also has a base link 64 that is configured to operably couple the sensor 52 to the elbow of the arm (not shown) as will be described in further detail below. The sensor 52 is positioned in the distal-most position in the forearm 50.

As best shown in FIGS. 3A and 3B, the base link 64 has a body 64A made up of two rod-like pieces 64A1, 64A2 (as best shown in FIG. 3A), an interface plate 64B at the distal end of the link 64, and an end plate 64C at the proximal end having a coupling component 64D. The interface plate 64B is configured to couple to the sensor 52. In one implementation, the plate 64B is rigidly coupled to the sensor 52. The body 64A has space between and adjacent to the rod-like pieces 64A1, 64A2 that can be configured to receive or provide space for on-board electronic components and wiring (not shown). The electronic components can include, but are not limited to, local motor driving boards, absolute positioning sensor boards, biometric sensor boards, and measurement boards to access the sensor data collected by the sensor 52. The coupling component 64D is configured to couple to the elbow joint (not shown) and/or the upper arm (not shown) of the device. In one embodiment, the coupling component 64D as shown is a projection 64D that defines a circular hole configured to receive and couple to an articulate shaft (not shown) of the upper arm (not shown). Alternatively, the coupling component 64D can be any known mechanism, component, or apparatus for coupling a forearm to an upper arm or elbow of a medical device.

In one implementation, the base link 64 is physically separate from and not rigidly coupled to the motor housing 54. This separation of the two components allows forces applied to the grasper 62 to be transferred through the front plate 56 and into the sensor 52 and reduces the diffusion of such forces. According to certain embodiments, the base link 64 is a cantilevered link 64 that allows the sensor 52 to measure the force applied on the arm 50, and in some cases, the distal endpoint of the end effector 62. Alternatively, the link 64 need not be a cantilevered link 64, but instead can have one or more components that apply a known amount of force thereon. Regardless, the base link 64 allows the sensor 52 to accurately measure the force of interest.

As best shown in FIG. 3C, the motor configuration made up of the two motors 58, 60 is similar to a grasper end effector motor configuration as disclosed in U.S. Provisional Application 61/663,194, filed on Jun. 22, 2012, which is hereby incorporated herein by reference in its entirety. In this particular embodiment, the motor 60 is an open/close motor 60 that is rotationally fixed to motor gear 66, which is threadably coupled to driven gear 68, which is supported by two bearings 70A, 70B. In one embodiment, the bearings 70A, 70B are constrained by the motor housing 54. The driven gear 68 defines a lumen (not shown) having internal threads (not shown). An externally-threaded drive rod 72 is positioned in the lumen of the driven gear 68 such that the driven gear 68 is operably coupled to the rod 72. Due to the coupling of the internal threads of the driven gear 68 with the external threads of the rod 72, rotation of the driven gear 68 causes the drive rod 72 to move laterally back and forth along the longitudinal axis of the drive rod 72. The drive rod 72 is operably coupled to the grasper arms 62A, 62B at the pivot point 74 on the grasper yoke 76 such that the lateral movement of the drive rod 72 causes the grasper arms 62A, 62B to open and close.

The motor 58 is a rotational motor 58 that is rotationally fixed to motor gear 78, which is threadably coupled to driven gear 80, which is supported by two bearings 82A, 82B. In one embodiment, the bearings 82A, 82B are constrained by the motor housing 54. The driven gear 80 is rotationally fixed to the grasper yoke 76, which is rotationally fixed to the grasper arms 62A, 62B such that rotation of the rotational motor 58 causes rotation of the grasper tool 62.

In one embodiment, the motors 58, 60 are both 6 mm motors. Alternatively, the motors 58, 60 are known brushed or brushless motors. The motors 58, 60 can be any motors ranging in size from about 2 mm to about 15 mm in diameter, so long as the motors 58, 60 provide sufficient force and speed profiles to achieve desired results. In accordance with one implementation, the motors 58, 60 are coreless brushed motors called 0615 (6 mm) or 0816 (8 mm), which are commercially available from Micromo, located in Clearwater, Fla. Alternatively, the motors 58, 60 are brushless motors called EC 6 mm and EC 10 mm, which are commercially available from Maxon Motor, located in Fall River, Mass. In a further alternative, the motors 58, 60 can be any known motors used in medical devices.

As mentioned above, in use, any force sensor disclosed or contemplated herein (including, for example, any one or more of the force sensors 22, 40, 52 discussed and depicted above, or one or more torque sensors as also discussed above) is configured to detect and collect the amount of force (or torque) applied by the arm or arms of a surgical device.

Figure 4:
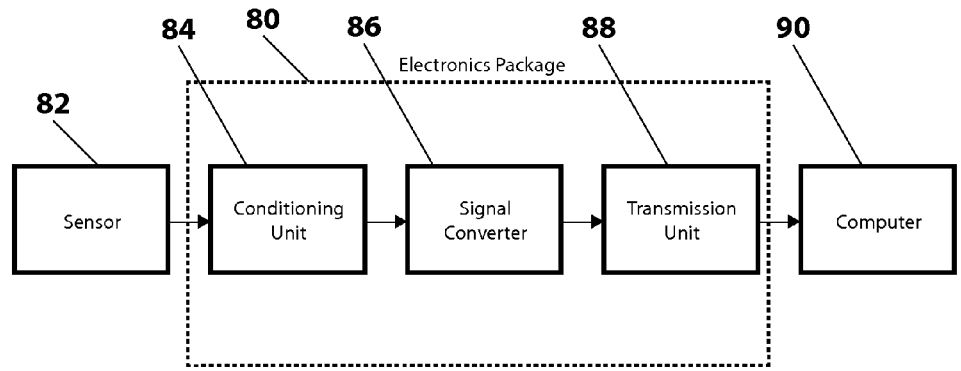
FIG. 4 is a schematic depiction of an electronics package relating to the output of data from a sensor, according to one embodiment.

As mentioned above, the information collected by the one or more sensors can then be outputted to a processor of some kind, such as a microprocessor in an external controller in communication with the surgical device. In one implementation, the data output occurs via an electronics package 80 as shown schematically in FIG. 4. In this embodiment, the representative single sensor 82 outputs (or transmits) analog or digital signals that are proportional to the amount of force detected by the sensor 82. The electronics package 80 can interpret and/or transmit these signals. The electronics package 80, according to one implementation, has a conditioning unit 84, a signal converting unit 86, and a transmission unit 88. It is understood that the sensor 82, the conditioning unit 84, the signal converting unit 86, the transmission unit 88, and computer 90 are all coupled to each other via at least one communication line. The communication line can be any line that can be used to carry signals from one component to another.

The conditioning unit 84 is configured to provide more robust or easier-to-detect signals. According to one embodiment, the conditioning unit 84 can be figured to filter, shift, amplify, or provide any other conditioning procedure to signals. The signal converting unit 86 is configured to convert analog signals to digital signals so that they can be used in a digital processor or computer. According to one embodiment, the signal converting unit 86 is an analog-to-digital converter ("ADC"). The transmission unit 88 is configured to transmit the signals from the electronics package 80 to the computer 90.

In one implementation, if the output signals from the sensor 82 are digital signals, they can be transmitted or outputted to the conditioning unit 84 (where they are amplified or otherwise conditioned) and then transmitted directly to the transmission unit 88, which transmits the signals to the computer 90. Alternatively, in those embodiments in which the output signals are analog, the signals can be conditioned via the conditioning unit 84 and also converted into digital signals via the signal converting unit 86 before being transmitted by the transmission unit 88 to the computer 90.

For purposes of this application, it is understood that the term "computer" is intended to mean any device that can be programmed to carry out arithmetic or logical operations. As such, "computer" encompasses any microprocessor, digital signal processor, or any other computer platform. This obviously would include any microprocessor, processor, or other type of computer incorporated into any external controller or user interface that is operably coupled to the surgical device.

According to one embodiment, the electronics package 80 is positioned on or in the surgical device (such as either of devices 10 or 30 as discussed above) and the computer 90 is positioned at a location that is external to the surgical device and the patient. Alternatively, both the electronics package 80 and the computer 90 are positioned on or in the robot. In yet another alternative, both the electronics package 80 and the computer 90 are positioned at some location external to the surgical device.

The computer 90 is configured to utilize the data for many end-user applications, including, for example, haptics, data collection for surgeon performance analytics, or for training purposes where the data is recorded and played back to trainees. In certain embodiments, the computer 90 uses the data to calculate the amount of force applied at the endpoint of one of the arms on the surgical device. Alternatively, the computer 90 can calculate the amount of force at any point on either of the arms.

In a further embodiment, the data can also be used for implementing methods of controlling the surgical device. That is, the information relating to the amount of force being applied by an arm of a device can be used to control that arm. In one example, if the arm contacts a cavity wall or an organ in the cavity, the force sensor 82 will sense the force applied to the arm as a result of this contact and the computer 90 can utilize that information to actuate the arm to perform some action to remedy the problem. For example, the computer 90 can actuate the arm to stop moving, shut down, reposition itself away from the point of contract, or take any other action to correct the problem. Various control methods that can be used by the computer 90 include force control, hybrid (force and position) control, admittance control, impedance control, or any combination of these or other known methods. In some embodiments, these methods can be used in conjunction with any combination of the existing position, velocity, acceleration, or current (torque control) control methods.

According to another implementation, the computer 90 can be configured to transmit the data to one or more other computers that can utilize the data for any of the applications described above or other applications.

Figure 5A:
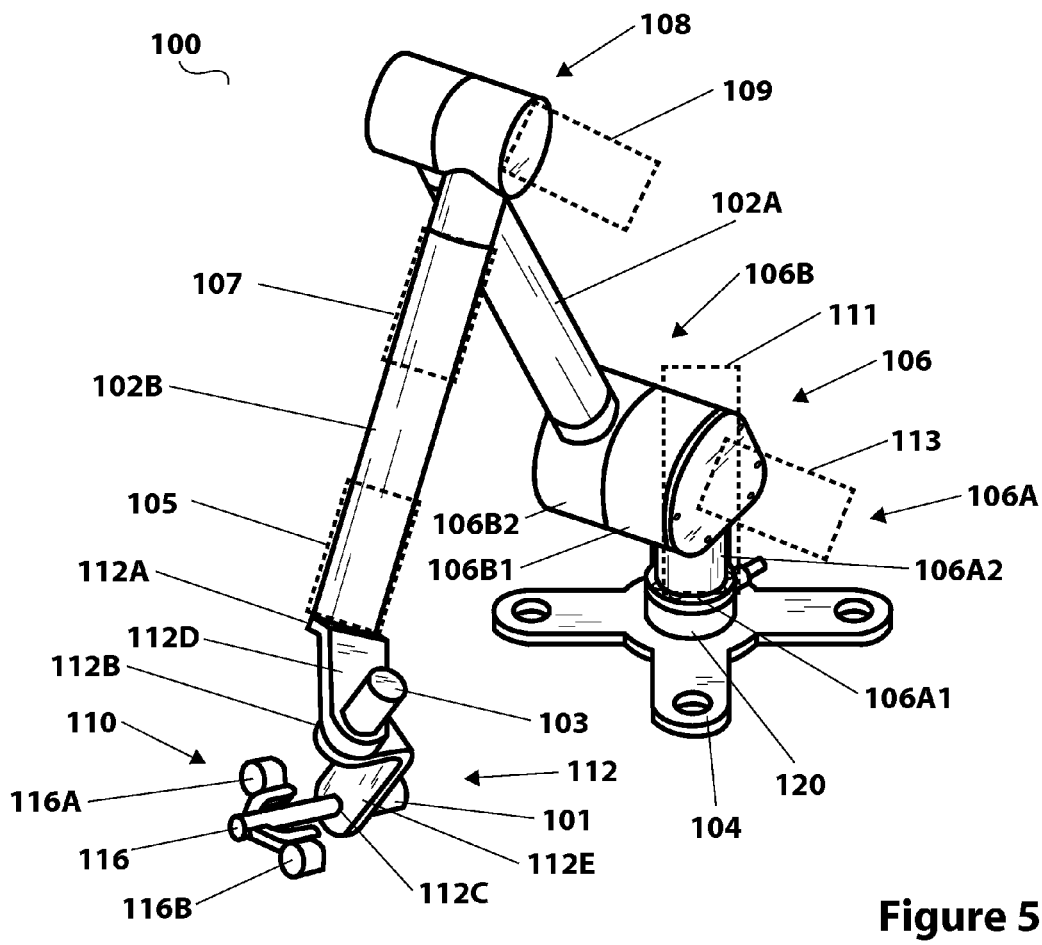
FIG. 5A is a perspective view of a controller, according to one embodiment.
Figure 5B:
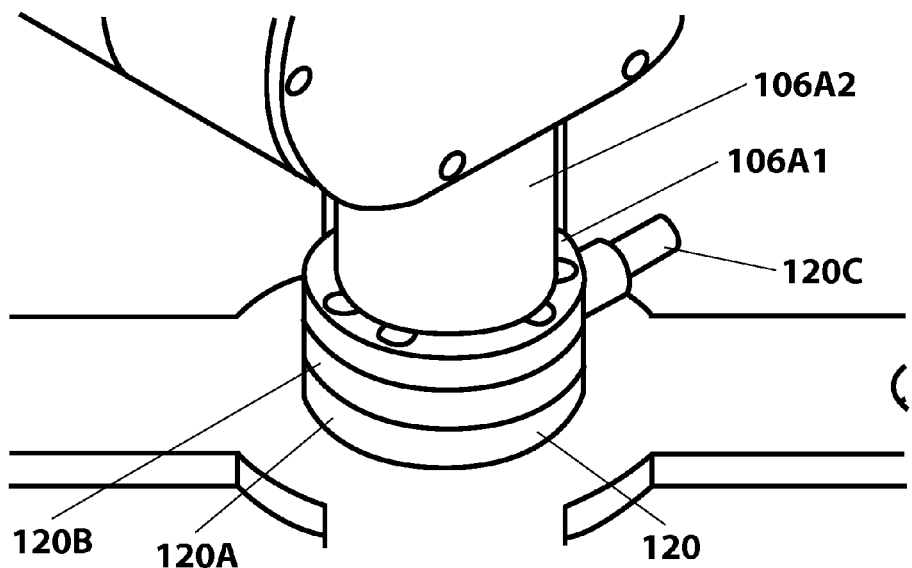
FIG. 5B is an exploded perspective view of a portion of the controller of FIG. 5A.
Figure 5C:
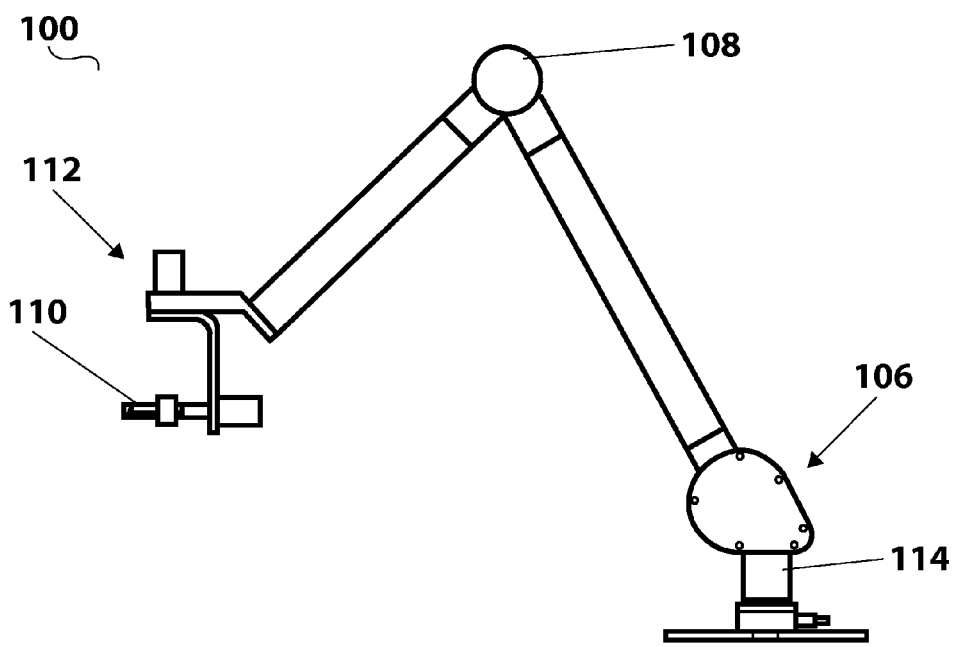
FIG. 5C is a side view of the controller of FIG. 5A.

Other embodiments of a surgical system relate to external controller embodiments having one or more force sensors (or other related types of sensors, such as torque sensors) that can be used to control a surgical device. FIGS. 5A, 5B, and 5C depict an external controller 100 having a known configuration similar to various commercial embodiments. This particular controller 100 has a controller arm 102 made up of an upper arm (also referred to as a first or upper link, rod, or tube) 102A and a forearm (also referred to as a second or lower link, rod, or tube) 102B. The upper arm 102A is rotatably coupled to a base 104 at a shoulder joint (also referred to as a first joint) 106 and the lower arm 102B is rotatably coupled to the upper arm 102A at an elbow joint (also referred to as a second joint) 108. A grasper 110 is rotatably coupled to the lower arm 102B at a wrist joint 112 and is configured to be grasped by a user (such as a surgeon).

As best shown in FIG. 5A, according to one implementation, the shoulder joint 106 is actually made up of two different joints: a rotating yaw joint 106A and a rotating pitch joint 106B. The rotating yaw joint 106A has a fixed joint component 106A1 coupled to the base 104 and a rotatable joint component 106A2 that is rotatably coupled to the fixed joint component 106A1 and rotates around an axis parallel to the longitudinal axis of the rotatable joint component 106A2 (and perpendicular to the plane of the base 104). The rotating pitch joint 106B has a fixed joint component 106B1 coupled to the rotatable joint component 106A2 and a rotatable joint component 106B2 that is rotatably coupled to the fixed joint component 106B1 and rotates around an axis parallel to the plane of the base 104.

Continuing with FIG. 5A, the wrist joint 112 is actually made up of three joints 112A, 112B, 112C. The first wrist joint 112A is a rotatable coupling at the lower arm 102B such that the wrist link 112D rotates around an axis parallel to the longitudinal axis of the lower arm 102B. The second wrist joint 112B is a rotatable coupling of the wrist link 112E to the wrist link 112D such that the wrist link 112E rotates around an axis that is perpendicular to the plane of the wrist link 112D. The third wrist joint 112C is a rotatable coupling of the grasper 110 to the wrist link 112E such that the grasper 110 rotates around an axis perpendicular to the plane of the wrist link 112E. These three joints 112A, 112B, 112C provide three axes of rotation. According to one implementation, the three axes of rotation of the three joints 112A, 112B, 112C all pass through a specific point.

In this embodiment, the grasper 110 has a pinch mechanism 116 made up of two finger loops 116A, 116B. In one implementation, the grasper 110 has a configuration that is substantially similar to the grasper used in the Da Vinci® system.

The controller 100 in this implementation also has motors that operate to provide haptic feedback. More specifically, the shoulder joint 106 has at least one motor positioned within the joint 106 (or otherwise operably coupled thereto). In one example, the motor 111 is coupled to or positioned within the joint 106 and operably coupled to the joint 106 such that the motor 111 can actuate the movement of the rotating yaw joint 106A. In another example, the motor 113 is coupled to the joint 106 and operably coupled thereto such that the motor 113 can actuate the movement of the rotating pitch joint 106B. Similarly, the elbow joint 108 also has at least one motor positioned within the joint 108 (or otherwise operably coupled thereto). In one example, the motor 109 is coupled to the joint 108 as shown. Alternatively, the motor 107 is disposed within the forearm 102B and operably coupled to the joint 108. Further, the wrist joint 112 can also have one or more motors operably coupled to one or more of the wrist joints 112A, 112B, 112C. For example, a motor 105 can be disposed within the forearm 102B that is operably coupled to the wrist link 112D such that the motor 105 can actuate the movement of the wrist link 112D. Alternatively, a motor 103 can be operably coupled to the wrist joint 112B to actuate the movement of the wrist link 112E. In a further alternative, a motor 101 can be operably coupled to the wrist joint 112C to actuate the movement of the grasper 110. In operation, it is understood that the motors are used to provide haptic feedback to the user or surgeon during a procedure. That is, the one or more force sensors (or torque sensors), such as any of the sensors discussed above, operably coupled to the surgical device sense force applied to at least one arm of the device (or torque at one or more joints) and that information is transmitted back to a processor as discussed above. The processor can use that information to calculate the force or torque being applied and transmit instructions based on that information to the motors in the controller 100 to actuate those motors to generate similar force or torque in the controller 100 that can be felt by the user or surgeon at the grasper 110, thereby giving the user or surgeon feedback in the form of force (resistance) similar to the feedback the surgeon or user would receive if she or he was holding the actual surgical device component experiencing the force.

In one embodiment, the motors in the controller 100 are known brushed or brushless motors. The motors can be any motors ranging in size from about 4 mm to about 30 mm in diameter, so long as the motors provide sufficient force and speed profiles to achieve desired results. In accordance with one implementation, the motors are any motors within that size range that are commercially available from Micromo, located in Clearwater, Fla. or from Maxon Motor, located in Fall River, Mass. In a further alternative, the motors can be any known motors of appropriate size used in medical devices or related controller components.

According to one implementation as best shown in FIG. 5B, the controller 100 has a force sensor 120 associated with the shoulder joint 106. More specifically, in one embodiment, the sensor 120 has a first component 120A coupled to the base 104 and a second component 120B coupled to the fixed joint component 106A1. In use, the sensor 120 detects any force applied to either the fixed joint component 106A1 or the base 104. The sensor 120 also has a connection component 120C that extends from the sensor 120 to a computer or other type of processor. Alternatively, one or more sensors can be positioned anywhere on or within the controller 100 at any location between the base 104 and the finger loops 116A, 116B. In accordance with another aspect, a single six-axis force sensor is positioned within or coupled to the yaw joint 106A (like sensor 120) and a separate sensor (not shown) is positioned on the grasper 110. Using analytical or iterative methods, force data from the sensor 120 at the yaw joint 106A and known information about the structural parameters of the controller 100 can be used by a processor to determine internal and external forces while the separate sensor on the grasper 110 can be used to determine grasping pressures or other relevant information. In a further implementation, separate sensors can be positioned at every joint 106, 108, 112 and provide feedback. In yet another embodiment, a single sensor is positioned somewhere on or operably coupled to the grasper 110.

In operation, it is understood that the one or more force sensors on the controller 100 are configured to sense force applied to the controller 100 by the user or surgeon, and that information is transmitted back to a processor as discussed above. The processor can use that information to calculate the force or torque being applied at the controller 100 and take that information into account for purposes of creating appropriate haptic feedback to the user at the controller 100 using the one or more motors described above that are operably coupled to the controller 100, thereby helping to ensure that the appropriate amount of force is being applied to the user's hand during use of the controller 100.

It is understood that the one or more sensors used with a controller (such as the controller 10) can be any of the force or torque sensors discussed above in relation to the surgical device embodiments. It is further understood that one or more sensors can be operably coupled in a similar fashion in similar configurations with any known controller having any known configuration that is capable of at least one directional force.

Figure 6:
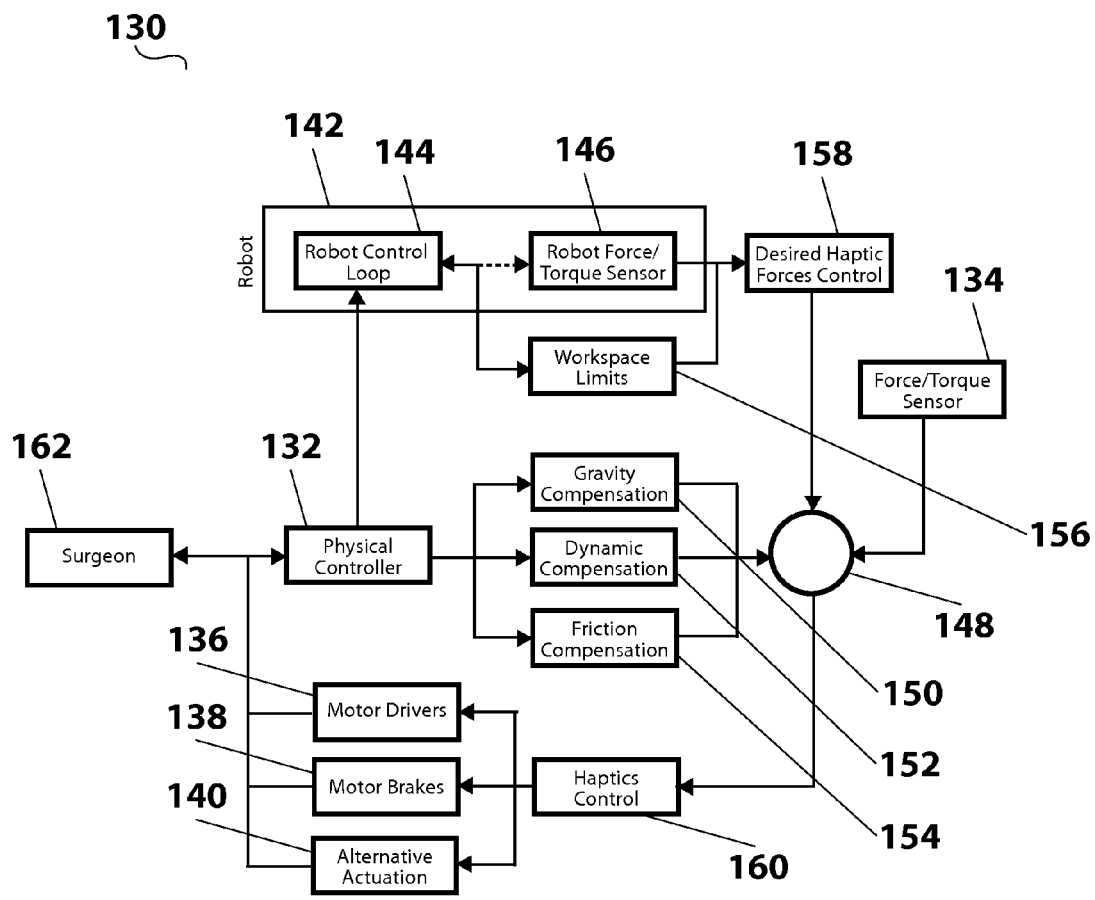
FIG. 6 is a schematic flow chart relating to a surgical system having an external controller and a robotic device, according to one embodiment.

FIG. 6 depicts a schematic representation of a surgical system 130 having an external controller 132 that is operably coupled to a surgical device 142. The external controller 132 can be any known controller (including, for example, the controller 100 discussed above) having at least one force sensor 134, along with at least one set of actuators or motors chosen from at least one of the following: motor drivers 136, motor brakes 138, and/or some other known type of actuators 140. The surgical device 142 can be any known surgical device (including, for example, either of the devices 10, 30 discussed above) having a control system 144 (typically in the form of a microprocessor or other type of computer) and at least one force sensor 146. As a result, this system 130 allows a surgeon 162 (or other user) to use the controller 132 to operate the surgical device 142 while the force sensors 134, 148 provide the system with force information that allows the system to provide haptic feedback to the surgeon 162 through the controller 132.

In use, the surgeon manipulates the controller 132 to control the surgical device 142. As a result of that manipulation, the controller 132 transmit information to the control system 144 in the surgical device 142. In one embodiment, the information transmitted by the controller 132 constitutes measurements relating to the physical position of the arm (or arms) of the controller 132. The information is used by the control system 144 to actuate the arm (or arms) of the surgical device 142 to move as desired by the surgeon 162. The force sensor 146 operates as discussed above with respect to sensors 22, 40, 52 by sensing the force applied to the device 142. In this implementation, the sensor 146 outputs that information to a haptic control process or application 158 running on a processor or computer 148 (which can be the same as the computer 90 discussed above or a similar processor, microprocessor, or computer) to determine the desired haptic forces (the amount of feedback force desired to be provided to the surgeon 162) via known methods such as, for example, proportional or exponential force feedback, impedance control, admittance control, or hybrid control.

According to one embodiment, the workspace limitations of the surgical device 142 can also be taken into account in this system 130. That is, the workspace limitation information can be saved in the device control system 144 (and provided to the haptic control algorithms 158) or it can be stored in the processor 148. In one embodiment, the information is modeled as an inward force that simulates a wall. Regardless, the information is used to transmit information to the controller that actuates one or more of the actuators 136, 138, 140 to generate forces at the controller 132 that help to prevent the surgeon 162 from exceeding the workspace of the surgical device 142. In one embodiment, the information actuates the actuator(s) 136, 138, 140 to provide direct force or vibration at the controller 132. Alternatively, the system can provide visual cues to the surgeon 162.

In one implementation, the computer 148 can also be configured to compensate for the outside forces in the system caused by gravity, friction, and inertia. That is, the force sensor 134 associated with the controller 132 detects and collects information about all forces being applied to the controller 132, not just the forces applied by the surgeon 162. This force information is provided to the computer 148 in one lump sum that includes all such forces. In this embodiment, the system 130 can take one or more of the outside forces into account and compensate for or "cancel out" those outside forces.

For example, one implementation of the system 130 allows for compensation for gravity. That is, the processor 148 can use structural and positional information about the controller 132 to calculate the effect of gravity on the controller 132 and effectively "subtract" that amount of force or otherwise "cancel out" that amount of force from the force detected by the sensor 134. As a result, in an ideal embodiment of the system 130, when the surgeon removes her hands from the controller 132, the controller 132 should not fall but instead should appear weightless as a result of the compensation for gravity.

Another implementation allows for dynamic compensation. That is, the processor 148 can use structural and positional information about the controller 132 to calculate the effect of inertia and other dynamic forces on the controller 132 during use and effectively "subtract" or otherwise "cancel out" that amount of force from the force detected by the sensor 134. As a result, rapid movements by the surgeon 162 would not create reaction forces provided as haptic feedback to the surgeon 162 and the effect would be that the mass of the controller 132 would not impose any forces on the system 130.

In a further embodiment, the system 130 can allow for friction compensation. That is, the processor 148 can use one or more force sensors in the controller 132 to detect any unexpected forces experienced by the controller 132 when force is applied to the handles of the controller 132 by the surgeon 162. Those unexpected forces can then be effectively "subtracted" from the force detected by the sensor 134. The result is a frictionless system that exhibits little resistance to movement.

In one embodiment, the system 130 can have only one form of compensation, such as, for example, gravity compensation. Alternatively, the system 130 can have two forms of compensation. In a further alternative, the system 130 can compensate for all three types of external forces: gravity, dynamic forces, and friction.

Once the computer has added up the total amount of the outside/unwanted forces to be compensated for, that amount is subtracted from the total amount of force information provided by the force sensor 134. The result of the calculation is the "error" between the amount of force actually applied to the controller 132 by the surgeon 162 and the amount of force that was desired. Information about this "error" amount is provided to a haptic control system or application 160 that actuates one or more of the actuators (the motor drivers 136, the motor brakes 138, and/or the other actuators) in the controller 132 to add or subtract that amount of force needed based on the error, thereby providing the haptic feedback to the surgeon 162. Hence, the haptic control system 160 determines the appropriate amount of haptic forces to generate in the controller 132.

Figure 7:
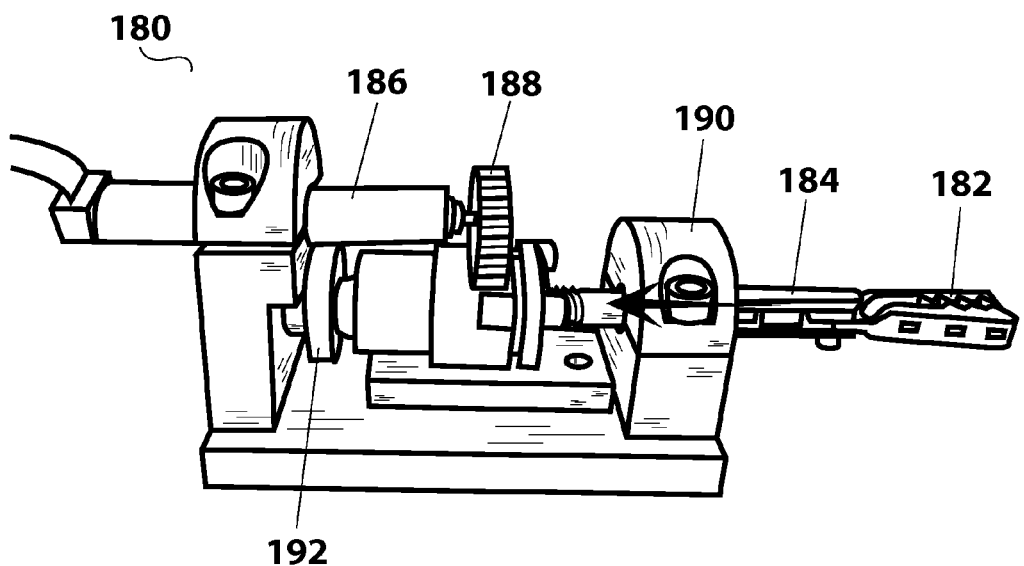
FIG. 7 is a perspective view of an arm of a robotic surgical device with a force sensor, according to one embodiment.

Another force-sensing grasper 180 embodiment is depicted in FIG. 7. In this implementation, the force being measured is the force applied along the drivetrain of the end effector. That is, the force sensor is integrated into the actuation component(s) or motor(s) of the end effector to measure directly the force applied by that component/motor (those components/motors) to the end effector. The end effector 180 is configured to transmit force feedback information to the surgical system, wherein the force feedback information is any information relating to the force which the end effector 180 is applying during use of the end effector 180. In certain implementations, this information can be used to adjust the amount of force being applied when it is determined that the force is too great or insufficient for the action being performed.

In this specific embodiment as shown, as mentioned above, the end effector 180 is a grasper end effector 180 having a grasper tool 182. The actuation system provided for this grasper end effector 180 in the embodiment as shown is merely an exemplary, known system and constitutes only one of many types and configurations of actuation systems that can be used for actuating a grasper tool 182, including the various systems discussed in the embodiments above. As shown, the grasper end effector 180 is configured to have two degrees of freedom. That is, the grasper tool 182 rotates about its long axis and moves between an open configuration and a closed configuration. To achieve movement of the grasper tool 182 between the open and closed configurations, the grasper end effector 180 has a shaft 184 that contains a threaded inner push/pull rod (not shown) that is coupled to the actuator or motor 186 (shown in FIG. 7 as a motor and gearhead) via the gears 188. The shaft 184 has an internal lumen (not shown) defined within the shaft 184, and the lumen has internal threads that match up with the external threads on the push/pull rod (not shown). In use, the motor 186 actuates the rotation of the gears 188, which causes the inner push/pull rod (not shown) to rotate. In contrast, the shaft 184 is restrained such that it cannot rotate. In one embodiment, the shaft 184 is fixed rotationally via a clamp 190. Thus, the meshing of the threads of the rod with the internal threads of the shaft 184 means that the rotation of the rod within the restrained shaft 184 causes the rod to translate laterally, thereby causing the grasper tool 182 to move between its open and closed positions.

In one embodiment, the force-sensing grasper 180 operates to sense the amount of force being applied by the grasper tool 182 by measuring the amount of axial force being transmitted through the push/pull rod (not shown) in the shaft 184. More specifically, the device has a sensor 192 that is positioned such that it can measure the force generated through the coupling of the gears 188 and the push/pull rod (not shown) coupled to the shaft 184. That is, the sensor 192 is positioned in FIG. 7 such that it is operably coupled to a proximal portion of the push/pull rod. In one embodiment, the sensor 192 measures tension and compression. According to one exemplary implementation, the sensor 192 is a force sensor 192 that measures axial loading. For example, the sensor 192 can be one of the ELFS Series of load cells available from Entran Sensors & Electronics in Fairfield, N.J. Alternatively, the sensor 192 can be any known type of force sensor.

Figure 8:
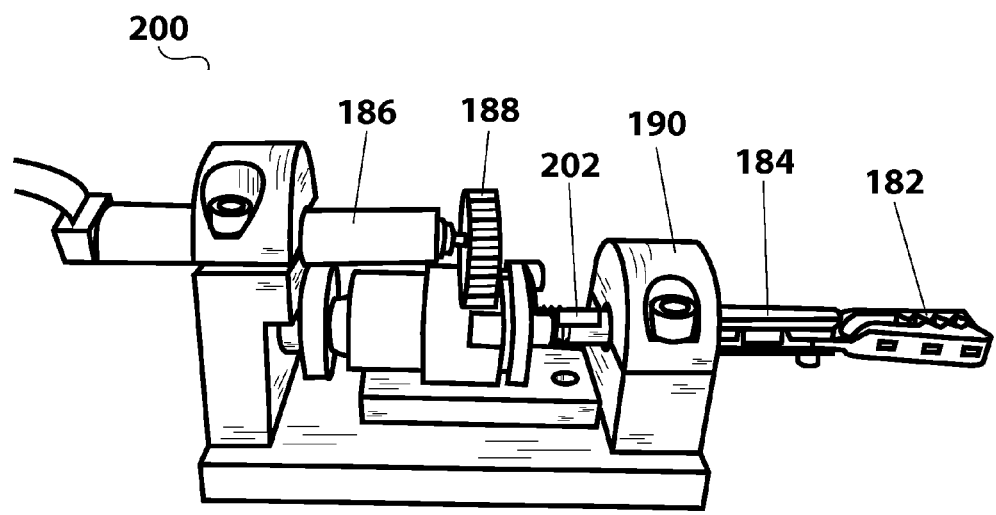
FIG. 8 is a perspective view of an arm of a robotic surgical device with a force sensor, according to another embodiment.

FIG. 8 depicts another embodiment of a force-sensing end effector 200. In this embodiment, the sensor 202 is positioned on the push/pull rod (not shown) proximal to the clamp 190. In one embodiment, the sensor 202 is positioned on or in operable coupling with the push/pull rod (not shown) within the shaft 184. Alternatively, the sensor 202 is positioned on or externally to the shaft 184, but still operably coupled to the push/pull rod. The sensor 202 is configured to measure the force applied to the push/pull rod (not shown).

Figure 9:
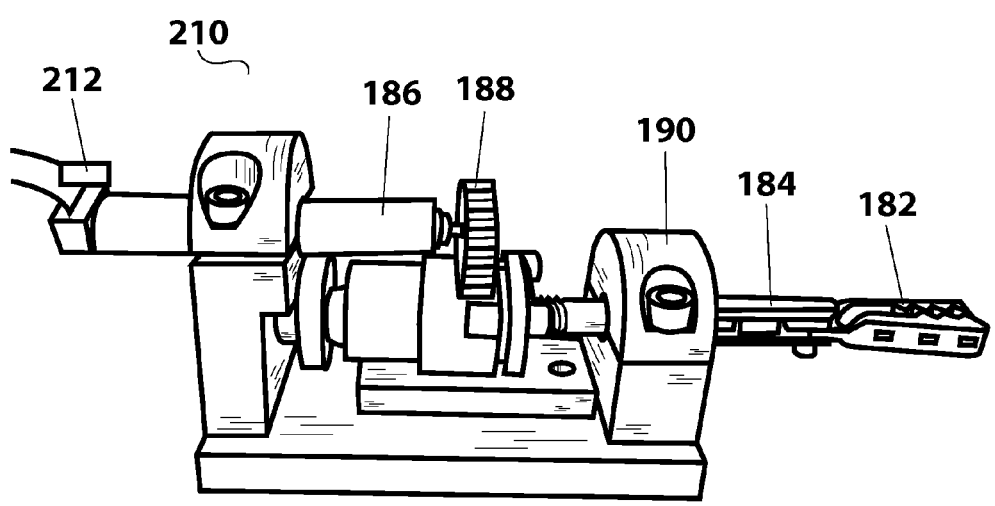
FIG. 9 is a perspective view of an arm of a robotic surgical device with a force sensor, according to a further embodiment.

FIG. 9 depicts yet another implementation of a force-sensing end effector 210. In this embodiment, the sensor 212 is operably coupled to the motor 186 such that the sensor 212 measures the current consumed by the motor 186. The information relating to the current can be used to determine the amount of force being applied by the grasper tool 182.

Figure 10A:
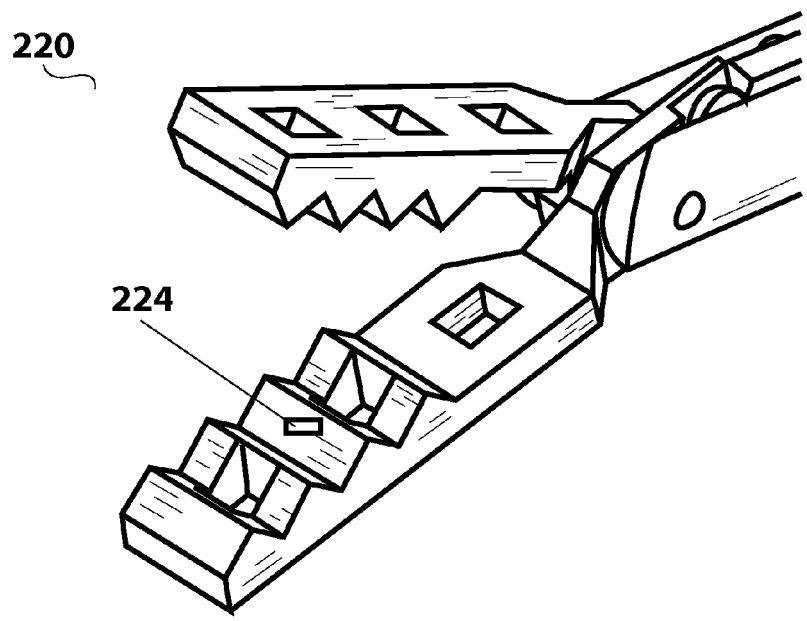
FIG. 10A is a perspective view of an end effector of a robotic surgical device with a force sensor, according to one embodiment.
Figure 10B:
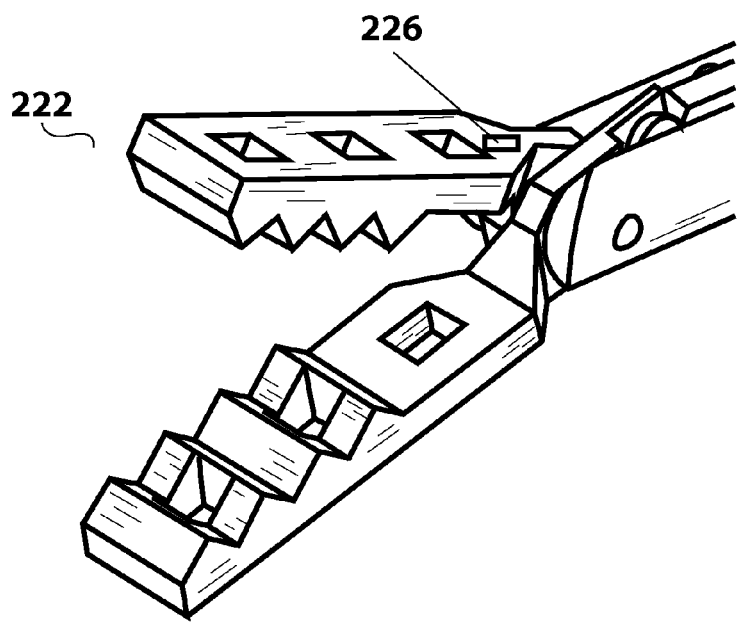
FIG. 10B is a perspective view of an end effector of a robotic surgical device with a force sensor, according to another embodiment.

FIGS. 10A and 10B depict two additional embodiments of force-sensing end effectors 220, 222 that measure contact force at the graspers (rather than measuring directly the force applied by the actuator(s)/motor(s)). In the embodiment shown in FIG. 10A, a sensor 224 is positioned on the grasper tool 182 itself. More specifically, the sensor 224 is positioned on the internal face of one of the two jaws of the tool 182 such that the sensor 224 measures the contact force on the internal face of the jaw. Alternatively, as shown in FIG. 10B, a sensor 226 can be positioned on an external face of a jaw of the grasper tool 182 near the pivot axis of the tool 182 such that the sensor 226 measures the deflection of the grasper. Using the deflection information, the force applied to the tool 182 can be determined.

Although the present invention has been described with reference to preferred embodiments, persons skilled in the art will recognize that changes may be made in form and detail without departing from the spirit and scope of the invention.

What is claimed is:

1. A robotic surgical system comprising:
   (a) a robotic surgical device configured to be positioned into a cavity of a patient through an incision, the device comprising:
      (i) a device body;
      (ii) at least one arm operably coupled to the body, wherein the at least one arm is configured to be positioned entirely within the cavity of the patient; and
      (iii) at least one sensor operably coupled to the device;
   (b) a processor operably coupled to the at least one sensor; and
   (c) a user controller operably coupled to the processor, the user controller comprising:
      (i) a base;
      (ii) an upper arm component operably coupled to the base at a shoulder joint, wherein the shoulder joint comprises a first actuator operably coupled to the processor;
      (iii) a forearm component operably coupled to the upper arm component at an elbow joint, wherein the elbow joint comprises a second actuator operably coupled to the processor; and
      (iv) a grasper operably coupled to the forearm component at a wrist joint, wherein the wrist joint comprises a third actuator operably coupled to the processor,
   wherein the at least one sensor is configured to sense force or torque at the robotic surgical device and transmit force or torque information to the processor,
   wherein the processor is configured to calculate the force or torque being applied at the robotic surgical device and transmit instructions to actuate at least one of the first, second, or third actuator based on the force or torque, thereby providing haptic feedback at the controller.

2. The robotic surgical system of claim 1, wherein the at least one sensor is a force sensor operably coupled to the at least one arm.

3. The robotic surgical system of claim 1, wherein the at least one sensor is a torque sensor operably coupled to a joint of the at least one arm.

4. The robotic surgical system of claim 1, wherein the at least one sensor is a force sensor positioned between the device body and the at least one arm.

5. The robotic surgical system of claim 1, wherein the at least one sensor is a force sensor disposed within the device body.

6. A robotic surgical system comprising:
   (a) a robotic surgical device comprising:
      (i) a device body configured to be positioned through an incision into a cavity of a patient;
      (ii) a first shoulder component operably coupled to the device body;
      (iii) a first arm operably coupled to the first shoulder component, wherein the first arm is configured to be positioned entirely within the cavity of the patient; and
      (iv) a sensor operably coupled to the device,
   wherein the device body is configured to be disposed in the incision when the first arm is positioned within the cavity;
   (b) a processor operably coupled to the sensor; and
   (c) a user controller operably coupled to the processor, the user controller comprising:
      (i) a base;
      (ii) a controller upper arm component operably coupled to the base at a shoulder joint, wherein the shoulder joint comprises a first actuator operably coupled to the processor;
      (iii) a controller forearm component operably coupled to the controller upper arm component at an elbow joint, wherein the elbow joint comprises a second actuator operably coupled to the processor; and
      (iv) a grasper operably coupled to the controller forearm component at a wrist joint, wherein the wrist joint comprises a third actuator operably coupled to the processor,
   wherein the sensor is configured to sense force or torque at the robotic surgical device and transmit force or torque information to the processor, and
   wherein the processor is configured to calculate the force or torque being applied at the robotic surgical device and transmit instructions to actuate at least one of the first, second, or third actuator based on the force or torque, thereby providing haptic feedback at the controller.

7. The robotic surgical system of claim 6, wherein the sensor is disposed between the device body and the first shoulder component.

8. The robotic surgical system of claim 6, wherein the sensor is disposed on the first arm.

9. The robotic surgical system of claim 8, wherein the first arm comprises a first arm upper arm component and a first arm forearm component, wherein the sensor is disposed on the first arm forearm component.

10. The robotic surgical system of claim 6, wherein the first arm comprises a first arm upper arm component and a first arm forearm component, wherein the first arm forearm component is operably coupled to the first arm upper arm component at an elbow joint, wherein the first arm forearm component comprises a link operably coupled at a distal end to the force sensor and operably coupled at a proximal end to the elbow joint.

11. The robotic surgical system of claim 10, further comprising an interface plate disposed between the force sensor and the link.

12. The robotic surgical system of claim 6, wherein the sensor is positioned to measure the amount of force applied at a distal-most point on the first arm.

13. A robotic surgical system comprising:
   (a) a robotic surgical device comprising:
      (i) a device body configured to be positioned through an incision into a cavity of a patient;
      (ii) a first arm operably coupled to the device body, the first arm comprising an arm actuator disposed within the first arm, wherein the first arm is configured to be positioned entirely within the cavity of the patient;
      (iii) a sensor operably coupled to the arm actuator; and
      (iv) an end effector operably coupled to the arm actuator, the end effector positioned at a distal end of the first arm;
   (b) a processor operably coupled to the sensor; and
   (c) a user controller operably coupled to the processor, the user controller comprising:
      (i) a base;

(ii) a controller upper arm component operably coupled to the base at a shoulder joint, wherein the shoulder joint comprises a first actuator operably coupled to the processor;

(iii) a controller forearm component operably coupled to the forearm upper arm component at an elbow joint, wherein the elbow joint comprises a second actuator operably coupled to the processor; and (iv) a controller grasper operably coupled to the controller forearm component at a wrist joint, wherein the wrist joint comprises a third actuator operably coupled to the processor, wherein the sensor is configured to sense force or torque at the robotic surgical device and transmit force or torque information to the processor, wherein the processor is configured to calculate the force or torque being applied at the robotic surgical device and transmit instructions to actuate at least one of the first, second, or third actuator based on the force or torque, thereby providing haptic feedback at the controller.

14. The robotic surgical system of claim 13, further comprising a push/pull rod comprising a distal portion and a proximal portion, wherein the push/pull rod is operably coupled to the arm actuator at the proximal portion and further wherein the push/pull rod is operably coupled to the end effector at the distal portion.

15. The robotic surgical system of claim 14, wherein the sensor is disposed proximal to the arm actuator and is operably coupled to the proximal portion of the push/pull rod.

16. The robotic surgical system of claim 14, wherein the end effector is a device grasper, wherein the device grasper comprises an open configuration when the push/pull rod is urged to a distal position, and further wherein the device grasper comprises a closed configuration when the push/pull rod is urged to a proximal position.

17. The robotic surgical system of claim 14, wherein the sensor is operably coupled to the push/pull rod such that the sensor is positioned along the length of the push/pull rod.

18. The robotic surgical system of claim 13, wherein the end effector is a device grasper.

19. The robotic surgical system of claim 13, further comprising a shaft operably coupled to the end effector and a first gear operably coupled to the shaft, wherein the arm actuator comprises a second gear operably coupled to the first gear.

20. The robotic surgical system of claim 19, wherein actuation of the arm actuator causes the shaft to rotate, thereby causing the end effector to rotate.

* * * * *